(12) United States Patent
Sierad et al.

(10) Patent No.: US 11,034,928 B2
(45) Date of Patent: Jun. 15, 2021

(54) MODULAR BIOREACTOR, COMPLIANCE CHAMBER FOR A BIOREACTOR, AND CELL SEEDING APPARATUS

(71) Applicant: CLEMSON UNIVERSITY, Clemson, SC (US)

(72) Inventors: Leslie Sierad, Central, SC (US); Christopher Delaney, Winston-Salem, NC (US); Richard Pascal, III, Chapin, SC (US); Dan Simionescu, Pendleton, SC (US); Agneta Simionescu, Pendleton, SC (US)

(73) Assignee: Clemson University Research Foundation, Clemson, SC (US)

( * ) Notice: Subject to any disclaimer, the term of this patent is extended or adjusted under 35 U.S.C. 154(b) by 684 days.

(21) Appl. No.: 14/807,357

(22) Filed: Jul. 23, 2015

(65) Prior Publication Data

US 2016/0024452 A1    Jan. 28, 2016

Related U.S. Application Data

(60) Provisional application No. 62/028,055, filed on Jul. 23, 2014.

(51) Int. Cl.
*C12M 1/34* (2006.01)
*C12M 3/00* (2006.01)
(Continued)

(52) U.S. Cl.
CPC ............ *C12M 41/40* (2013.01); *C12M 21/08* (2013.01); *C12M 23/00* (2013.01); *C12M 23/44* (2013.01);
(Continued)

(58) Field of Classification Search
CPC ...... F04D 17/10; F04D 29/023; F04D 29/053; F04D 29/266; F04D 29/284;
(Continued)

(56) References Cited

U.S. PATENT DOCUMENTS 5,846,828 A    12/1998 Peterson et al.
5,899,937 A     5/1999 Golstein et al.
(Continued)

OTHER PUBLICATIONS

Aleksieva, et al.; "Use of a special bioreactor for the cultivation of a new flexible polyurethane scaffold for aortic valve tissue engineering," *BioMedical Engineering Online*, 2012; 11, pp. 92. (20 pages).

(Continued)

*Primary Examiner* — Gautam Prakash
*Assistant Examiner* — Lydia Edwards
(74) *Attorney, Agent, or Firm* — Dority & Manning, P.A.

(57) ABSTRACT

Bioreactors and components of bioreactors are described as may be beneficially utilized in development and conditioning of cellular materials for study or implant. The bioreactors are modular and components of the bioreactors can be easily assembled with alternatives provided to develop specific, predetermined conditioning environments for cellular materials (e.g., implantable tissue). By selection of one of multiple alternative compliance chambers, a bioreactor can be utilized to condition tissue in a low pressure circuit (e.g., a pulmonary heart circuit), and by utilization of an alternative compliance chamber, the bioreactor can instead condition tissue in a high pressure circuit (e.g., an aortic heart circuit).

23 Claims, 9 Drawing Sheets

(51) Int. Cl.
C12M 1/00 (2006.01)
C12M 1/42 (2006.01)
(52) U.S. Cl.
CPC ............ *C12M 29/00* (2013.01); *C12M 29/12* (2013.01); *C12M 35/04* (2013.01)
(58) Field of Classification Search
CPC ................. F04D 29/626; F04D 29/642; F05D 2300/171; F05D 2300/174; F05D 2300/43; F05D 2300/603; C12M 21/08; C12M 23/00; C12M 23/44; C12M 29/00; C12M 29/12; C12M 35/04; C12M 41/40
USPC .............................................. 435/289.1, 325
See application file for complete search history.

(56) References Cited

U.S. PATENT DOCUMENTS

| | | | |
|---|---|---|---|
| 6,121,042 A * | 9/2000 | Peterson | C12M 41/00 435/284.1 |
| 6,126,007 A | 10/2000 | Kari et al. | |
| 6,383,732 B1 | 5/2002 | Stone | |
| 6,409,758 B2 | 6/2002 | Stobie et al. | |
| 6,432,712 B1 | 8/2002 | Wolfinbarger, Jr. | |
| 6,652,583 B2 | 11/2003 | Hopkins et al. | |
| 6,702,852 B2 | 3/2004 | Stobie et al. | |
| 6,881,569 B2 | 4/2005 | Perry et al. | |
| 6,952,814 B2 | 10/2005 | Joseph et al. | |
| 6,964,682 B2 | 11/2005 | Nguyen-Thien-Nhon et al. | |
| 6,966,925 B2 | 11/2005 | Stobie | |
| 7,063,942 B2 | 6/2006 | Dancu et al. | |
| 7,112,218 B2 | 9/2006 | McAllister et al. | |
| 7,179,287 B2 | 2/2007 | Wofinbarger, Jr. | |
| 7,378,271 B2 | 5/2008 | Bader | |
| 7,439,057 B2 | 10/2008 | Frangos et al. | |
| 7,498,412 B2 | 3/2009 | Huang et al. | |
| 7,504,258 B2 | 3/2009 | McAllister et al. | |
| 7,645,568 B2 | 1/2010 | Stone | |
| 7,658,763 B2 | 2/2010 | Stobie | |
| 7,691,046 B2 | 4/2010 | Sullivan | |
| 7,744,526 B2 | 6/2010 | McAllister et al. | |
| 7,753,840 B2 | 7/2010 | Simionescu et al. | |
| 7,754,232 B2 | 7/2010 | Fisher et al. | |
| 7,819,915 B2 | 10/2010 | Stobie et al. | |
| 7,851,200 B2 | 12/2010 | More | |
| 7,871,367 B2 | 1/2011 | Anderson et al. | |
| 8,230,717 B2 | 7/2012 | Matonick | |
| 8,308,629 B2 | 11/2012 | Watschke et al. | |
| 8,399,243 B2 | 3/2013 | Bouten et al. | |
| 8,491,457 B2 | 7/2013 | Atala et al. | |
| 8,609,415 B2 | 12/2013 | Kortsmit et al. | |
| 2002/0146817 A1* | 10/2002 | Cannon | C12M 23/42 435/289.1 |
| 2013/0160577 A1* | 6/2013 | Williams | C12M 35/04 73/865.6 |

OTHER PUBLICATIONS

Baraki, et al.; "Orthotopic replacement of the aortic valve with decellularized allograft in a sheep model," *Biomaterials*; 2009; 30, pp. 6240-6246.

Barron, et al.; "Bioreactors for Cardiovascular Cell and Tissue Growth: A Review," *Annals of Biomedical Engineering*; 2003, 31, pp. 1017-1030.

Barzilla, et al.; "Design and Validation of a Novel Splashing Bioreactor System for use in Mitral Valve Organ Culture," *Annals of Biomedical Engineering*, 2010; 38 (11), pp. 3280-3294.

Berry, et al.; "Bioreactors for Development of tissue Engineered Heart Valves," *Annals of Biomedical Engineering*, 2010; 38 (11), pp. 3272-3279.

Bilodeau, et al.; "Bioreactors for Tissue Engineering: Focus on Mechanical Constraints. A Comparative Review," *Tissue Engineering*, 2006; 12 (8), pp. 2367-2384.

Bowles, et al.; "Hydrodynamic Evaluation of a Bioreactor for Tissue Engineering Heart Valve," *Cardiovascular Engineering and Technology*, Mar. 2010; 1 (1), pp. 10-17.

Brazile, et al.; "On the Bending Properties of Porcine Mitral, Tricuspid, Aortic, and Pulmonary Valve Leaflets," *Journal of Long-Term Effects of Medical Implants*; (2014); pp. 41-53.

Breuer, et al.; "Applications of Tissue-Engineering Principles toward the Development of a Semilunar Heart Valve Substitute," *Tissue Engineering*, 2004; 10 (1/2), pp. 1725-1738.

Butler, Ph.D. et al.; "Using Functional Tissue Engineering and Bioreactors to Mechanically Stimulate Tissue-Engineered Constructs," *Tissue Engineering*, 2009; 15 (4), pp. 741-751.

Caudle, N.; "The Matrix Reloaded," *Glimpse research and creative discovery*, Clemson University Magazine; Spring 2014, pp. 13-23.

Chow, et al.; "Mitigation of diabetes-related complications in implanted collagen and elastin scaffolds using matrix-binding polyphenol," *Biomaterials*, Jan. 2013; 34 (3), pp. 685-695.

Colazzo, et al.; "Extracellular matrix productionby adipose-derived stem cells: implications for heart valve tissue engineering," *Biomaterials*, 2011; 32 (1), pp. 119-127.

DeBorde, et al.; "Development of a Tissue Engineered Mitral Valve Scaffold," ISACB Presentation, Apr. 2014; 1 page.

Durst, et al.; "Design and Physical Characterization of a Synchronous Multivalve Aortic Valve Culture System," *Annals of Biomedical Engineering*; 2010, 38 (2), pp. 319-325.

Elman, et al.; "A comparison of adipose and bone marrow-derived mesenchymal stromal cell secreted factors in the treatment of systemic inflammation," *Journal of Inflammation* (London), 2014; 11 (1), pp. 1-8. [doi:10.1186/1476-9255-11-1].

Engelmayr, Jr., et al.; "A Novel Flex-Stretch-Flow Bioreactor for the Study of Engineered Heart Valve Tissue Mechanobiology," *Annals of Biomedical Engineering*; 2008, 36 (5), pp. 700-712.

Flanagan, et al.; "The in vitro development of autologous fibrin-based tissue-engineered heart valves through optimized dynamic conditioning," *Biomaterials*; 2007, 28, pp. 3388-3397.

Geeslin, et al.; "Bioreactor for the reconstitution of a decellularized vascular matrix of biological origin," *Journal Biomedical Science and Engineering*; 2011, 4, pp. 435-442.

Gheewala, et al.; "Design and Mechanical Evaluation of a Physiological Mitral Valve Organ Culture System," *Cardiovascular Engineering and Technology*; 2010, 1 (2), pp. 123-131.

Goldstein, et al.; "Functional Tissue Engineering Requires Bioreactor Strategies," *Tissue Engineering: Part A*; 2009, 15 (4), pp. 739-740.

Grande-Allen, et al.; "The heterogeneous biomechanics and mechanobiology of the mitral valve: implications for tissue engineering," *Curr. Cardiol. Reports*, 2011; 13 (2), pp. 113-120.

Hildebrand, et al.; "Design and Hydrodynamic Evaluation of a Novel Pulsatile Bioreactor for Biologically Active Heart Valves," *Annals of Biomedical Engineering*; 2004, 32 (8), pp. 1039-1049.

Hildebrand; "Design and Evaluation of a Novel Pulsatile Bioreactor for Biologically Active Heart Valves," *Paper Submitted to Graduate Faculty of School of Engineering—Univ. of Pittsburgh*; 2003, 187 pages.

Hoerstrup, et al.; "Tissue engineering of small caliber vascular grafts," *European Journal of Cardio-thoracic Surgery*; 2001, 20, pp. 164-169.

Hoerstrup, M.D., et al.; "Functional Living Trileaflet Heart Valves Grown in Vitro," *American Heart Association Inc.*; 2000, available at http://www.circulationaha.org. (6 pages).

Kaasi, et al.; "Using a VAD-Based Bioreactor to Host a Tissue Engineered Heart Valve," *21" Congresso Brasileiro de Engenharia Biomédica*; (Date Unknown), ISBN: 978-85-60064-13-7 (4 pages).

Karim, et al.; "The Cariovascular Tissue-Reactor: A Novel Device for the Engineering of Heart Valves," *Artificial Organs*; 2006, 30 (10), pp. 809-814.

Kennamer, Allison R..; "Interstitial Cell Seeding and Dynamic Conditioning of Aortic heart Valve Scaffolds," A Thesis—Graduate School, Clemson University; Dec. 2013; 77 pages.

Konduri, et al.; "Normal Physiological Conditions Maintain the Biological Characteristics of Porcine Aortic Heart Valves: An Ex Vivo Organ Culture Study," *Annals of Biomedical Engineering*; 2005, 33 (9), pp. 1158-1166.

(56) References Cited

OTHER PUBLICATIONS

Lee, M.S., et al.; "Endothelialization of Heart Valve Matrix Using a Computer-Assisted Pulsatile Bioreactor," *Tissue Engineering*; 2009, 15 (4), pp. 807-814.
Leo, et al.; "A Comparison of Flow Field Structures of Two Tri-Leaflet Polymeric Heart Valves," *Annals of Biomedical Engineering*; 2005, 33 (4), pp. 429-443.
Leo, et al.; "Fluid Dynamic Assessment of Three Polymeric Heart Valves using Particle Image Velocimetry," *Annals of Biomedical Engineering*; 2006, 34 (6), pp. 936-952.
Liao, et al.; "Effects of decellularization on mechanical and structural properties of the porcine aortic valve leaflets," *Biomaterials*; Mar. 2008; 29 (8); pp. 1065-1074.
Lichtenberg, et al.; "In vitro re-endothelialization of detergent decellularized heart valves under simulated physiological dynamic conditions," *Biomaterials*; 2006, 27, pp. 4221-4229.
Lieber, et al.; "Design of a Miniature Tissue Culture System to Culture Mouse Heart Valves," *Annals of Biomedical Engineering*; 2010, 3 (3), pp. 674-682.
Martin, et al.; "Bioreactors for tissue mass culture: Design, characterization, and recent advances," *Biomaterials*; 2005, 26, pp. 7481-7503.
Martin, et al.; "The role of bioreactors in tissue engineering," *Trends in Biotechnology*; 2004, 22 (2), 7 pages.
Miller; "Design and Development of a Novel Bioreactor for Tissue Engineered Heart Valves," *A Thesis Presentation—Arizona State University*; 2002, 136 pages.
Mol, et al.; "Tissue Engineering of Human Heart Valve Leaflets: A Novel Bioreactor for a Strain-Based Conditioning Approach," *Annals of Biomedical Engineering*; 2005, 33 (12), pp. 1778-1788.
Montoya, et al.; "Preparation of Ex Vivo-Based Biomaterials Using Convective Flow Decellularization," *Tissue Engineering, Part C*, 2009; 15 (2), pp. 191-193.
Morsi, PhD., et al.; "Development of a novel pulsatile bioreactor for tissue culture," *Jrnl. Artif. Organs*; 2007, 10, pp. 109-114.
Narita, M.D., et al.; "Novel Pulse Duplicating Bioreactor System for Tissue-Engineered Vascular Construct," *Tissue Engineering*; 2004, 10 (7/8), pp. 1224-1233.
Pascal, et al.; "Systems to Facilitate Adult Stem Cell Seeding of Aortic Heart Valve Scaffolds," Poster; *Department of Bioengineering; Clemson University*; (Nov. 15, 2012), 1 page.
Paz, et al.; "Tissue Engineered Trachea Using Decellularized Aorta," *Journal of Bioengineering & Biomedical Science*, 2011; S2:001. DOI: 10.4172/2155-9538.S2-001. (7 pages).
Ratcliffe, et al.; "Bioreactors and Bioprocessing for Tissue Engineering," *Ann. N.Y. Acad. Sci.*; 2002, 961, pp. 210-215.
Ruel, et al.; "A New Bioreactor for the Development of Tissue-Engineered Heart Valves," *Annals of Biomedical Engineering*; 2009, 37 (4), pp. 674-681.
Sarkar, et al.; "Addressing thrombogenicity in vascular graft construction," *Journal of Biomedical Materials Research, Part B Applied Biomaterials*, 2007; 82 (1), pp. 100-108
Sauer et al; "Thoughts and Progress," *Artificial Organs*; 2002, 26(8), pp. 703-733.
Schenke-Layland, et al.; "Complete dynamic repopulation of decellularized heart valves by application of defined physical signals—an in vitro study," *Cardiovascular Research*; 2003, 60, pp. 497-509.
Schliecher, et al.; "Simplified Pulse Reactor for Real-Time Long-Term In Vitro Testing of Biological Heart Valves," *Annals of Biomedical Engineering*, 2010, 38 (5), pp. 1919-1927.
Sierad, et al.; "Design and Testing of a Pulsatile Conditioning System for Dynamic Endothelialization of Polyphenol-Stabilized Tissue Engineered heart Vavles,"*Cardiovascular Engineering and Technology*; (Jun. 2010) vol. 1, No. 2, pp. 138-153.
Sierad, et al.; "Surface Modification, Endothelial Cell Coating, and Bioreactor Testing of Mechanical Heart Valves," PowerPoint—Clemson University, Clemson SC 29634; (2013); pp. 1-22.
Sierad, et al.; "Surface Modification, Endothelial Cell Coating, and Bioreactor Testing of Mechanical Heart Valves," Article; Clemson University, Clemson SC 29634; (May 2012); 1 page.
Sierad, et al.; "Surface Modification, Endothelial Cell Coating, and Bioreactor Testing of Mechanical Heart Valves," Poster Presentation; Clemson University, Clemson SC 29634; (2013); 1 page.
Sierad, et al.; "Bioreactor Technologies for Clinical Translation of Tissue Engineered Heart Valves," ISACB Article Presentation; Clemson University, Clemson SC 29634; (Apr. 2, 2014); 2 pages.
Sierad, L.N.; "A Pulsatile Bioreactor for Conditioning Tissue Engineered heart Valves," *A Thesis Presented to Graduate School of Clemson University*, May 2009; 95 pages.
Simionescu; "Form Follows Function: Advances in Trilayered Structure Replication for Aortic Heart Valve Tissue Engineering," *Journal of Healthcare Engineering*; 2012, 3, pp. 179-202.
Sodian, M.D., et al.; "New Pulsatile Bioreactor for Fabrication of Tissue-Engineered Patches," *J. Biomed. Mater. Res.*; 2001, 58, pp. 401-405.
Sodian, M.D., et al.; "Tissue Engineering Bioreactors: A New Combined Cell-Seeding and Perfusion System for Vascular Tissue Engineering," *Tissue Engineering*; 2002, 8(5), pp. 863-872.
Sodian, M.D., et al.; "Tissue Engineering of a Trileaflet Heart Valve—Early In Vitro Experiences with a Combined Polymer," *Tissue Engineering*; 1999, 5 (5), pp. 489-494.
Sodian, M.D., et al.; "Tissue Engineering of Heart Valves: In Vitro Experiences," *Ann. Thoracic Surgery*; 2000, 70, pp. 140-144.
Sodian, M.D., et al.; "Tissue-Engineering Bioreactors: A New Combined Cell-Seeding and Perfusion System for Vascular Tissue Engineering," *Tissue Engineering*; 2002, 8 (5), pp. 863-873.
Tedder, et al., "Stabilized Collagen Scaffolds for Heart Valve Tissue Engineering," *Tissue Engineering; Part A*; 2009, 15 (6), pp. 1257-1268.
Tedder, et al.; "Assembly and Testing of Stem Cell-Seeded Layered Collagen Constructs for Heart Valve Tissue Engineering," *Tissue Engineering; Part A*; 2011, 17, 1 and 2, pp. 25-38.
Warnock, et al.; "Design of a Sterile Organ Culture System for the Ex Vivo Study of Aortic Heart Valves," *Journal of Biomechanical Engineering*; Oct. 2005, 127, pp. 857-861.
Wendt, et al.; "Potential and Bottlenecks of Bioreactors in 3D Cell Culture and Tissue Manufacturing," *Advanced Materials*; 2009, 21, pp. 3352-3367.
Weston, et al.; "Biosynthetic Activity in Heart Valve Leaflets in Response to In Vitro Flow Environments," *Annals of Biomedical Engineering*; 2001, 29, pp. 752-763.
Zeltinger, PhD., et al.; "Development and Characterization of Tissue-Engineered Aortic Valves," *Tissue Engineering*; 2001, 7 (1), pp. 9-22.
Ziegelmueller, et al.; "Optical Monitoring During Bioreactor Conditioning of Tissue-Engineered Heart Valves," *Tissue Engineering*; 2010, 56, pp. 228-231.
Zou, PhD., et al.; "Mechanical Evaluation of Decellularized Porcine Thoracic Aorta," *Journal of Surgical Research*; 2012, 175, pp. 359-368.

\* cited by examiner

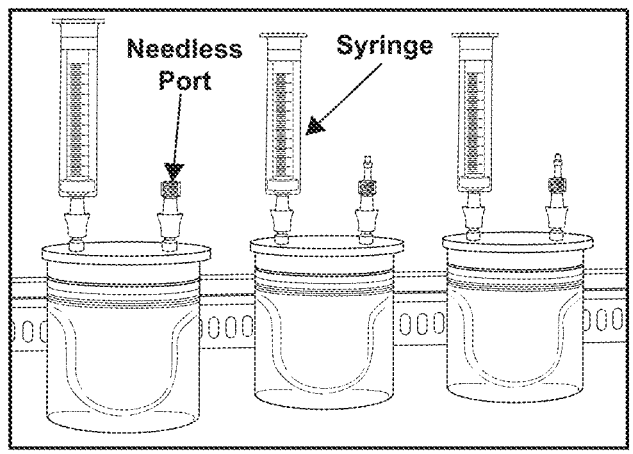
FIG. 17A
FIG. 17B
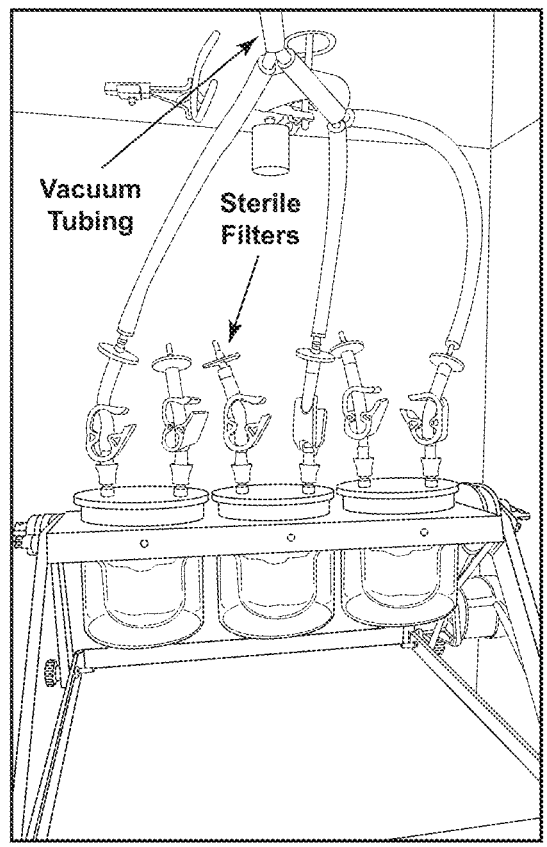
FIG. 17C
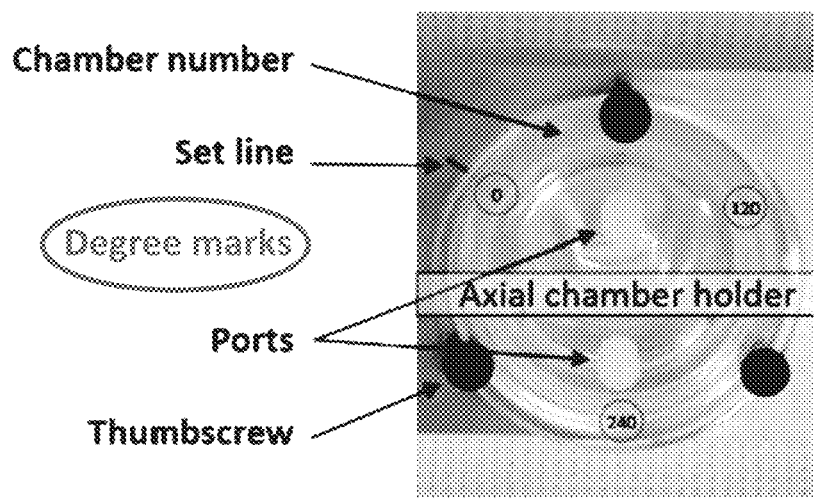
FIG. 18

MODULAR BIOREACTOR, COMPLIANCE CHAMBER FOR A BIOREACTOR, AND CELL SEEDING APPARATUS

CROSS REFERENCE TO RELATED APPLICATION

This application claims filing benefit of U.S. Provisional Patent Application Ser. No. 62/028,055 having a filing date of Jul. 23, 2014, which is incorporated herein in its entirety.

STATEMENT AS TO RIGHTS TO INVENTIONS MADE UNDER FEDERALLY SPONSORED RESEARCH

This invention was made with Government support under Grant No. RO1 HL 093399 awarded by the National Institutes of Health. The Government has certain rights in the invention.

BACKGROUND

Replacement of damaged or diseased tissue has become the standard of care for much pathology. For example, the pyrolytic carbon bileaflet mechanical valve that was designed in the 1970's has long been utilized for replacement of damaged or diseased heart valves. Unfortunately, thrombogenicity of the surfaces of synthetic implants remains a cause for much concern. For instance, non-biological devices such as mechanical heart valves introduce turbulent blood flow profiles. The turbulence can activate platelets that in turn initiate the formation of thrombi. To prevent this from occurring, patients are put on life-long anticoagulant therapy that involves the administration of a blood thinner such as Warfarin. Warfarin decreases the blood's ability to coagulate on the implant, but it also prevents coagulation systemically, leaving the patient vulnerable to major bleeding events. The reliance upon an expensive drug therapy and the necessity of close patient monitoring is undesirable and the main factor that has kept mechanical valve replacement out of developing countries.

Recent advances in the development of bioprosthetic and tissue engineered implants presents exciting possibilities for long-term treatments that require minimal follow-up care or drug therapies as compared to synthetic materials. For instance, bioprosthetic heart valves (BPVs) that are currently made from either porcine aortic valves or bovine pericardium do not require the expensive and life-long anticoagulant therapy that is necessary following implant of a mechanical heart valve. However, transplanted natural tissues (e.g., xenographic or allographic tissue) still present certain problems that must be overcome for wider use in the general population. For instance, BPVs are predicted to last 10-15 years, which is a lower expectation than that of mechanical valves.

Tissue engineering approaches have been developed that seek to provide long-term curative solutions to disease and tissue degeneration. The ideal constructs will not simply compensate for the damaged tissue; the aim is create living tissue that can be implanted into a human and will, from that point on, grow and remodel. Ideally, a tissue engineered implant will resemble both the size and shape of the native tissue; be durable and fully functioning with good hemodynamics; be non-immunogenic, non-inflammatory, non-thrombogenic, and non-obstructive; respond to mechanical and biological cues appropriately; grow in size with the recipient; and adapt to changing conditions throughout the life of the recipient and valve.

A key to achieving a long-term implant is the ability of the implanted tissue to repair itself, for instance in response to micro-tears. This requires the presence of cells to remodel the matrix as necessary. Multiple methods of creating such engineered tissues are being investigated and developed. Among the most researched and advanced methods are those that utilize an implantable scaffold that can be seeded with living cells, for instance a patient's own stem cells, or can accept in-growth of living cells following implantation. A major obstacle to the creation of such engineered tissues, particularly in use of biodegradable synthetic (e.g. polymer) scaffolding, is inadequate mechanical properties to withstand in vivo forces following implantation. Conversely, many stabilized natural tissue scaffolds have more than adequate mechanical properties, but are unable to degrade appropriately to facilitate the formation of a natural replacement or have chemical properties that do not facilitate cellular in-growth. As a result, research is being focused on decellularized natural tissue scaffolds that will allow the recipient patient's cells to infiltrate the extra-cellular matrix, repopulate the tissue, and eventually replace the slowly degrading donor scaffold with newly fabricated extra-cellular matrix.

Multiple groups have demonstrated cell seeding on the exterior surface of implantable tissues (e.g., heart valve cusps) and some interstitial seeding has even been achieved, though full revitalization has not been realized. Even if an implantable tissue scaffold can be successfully seeded with cells, it is likely the construct will need some sort of progressive conditioning to encourage the cells to remain attached and continue to grow and develop normally following implantation. Overall, more progress is needed to achieve full and consistent external and internal recellularization of implantable scaffolds and to determine what methods are needed to allow the cells to remain as well as to continue to thrive in an in vivo environment.

Many bioreactor systems have been proposed to develop, test and precondition tissue engineered constructs. Although many designs exist, few are able to simultaneously subject tissue to multiple physiological conditions such as flow characteristics and pressure. Those that can are very cumbersome to set up and operate for the duration of an experiment, especially while maintaining sterile conditions. Moreover, existing systems are operable over a fairly narrow range of operating conditions.

What is needed in the art are bioreactors and associated components that can be utilized in development and conditioning of implantable materials.

SUMMARY

According to one embodiment, disclosed is a compliance chamber for a bioreactor. The compliance chamber can include a fluid conduit that has a first end and a second, opposite end. The first end of the fluid conduit can be locatable in fluid communication with a circulatory flow path through the bioreactor and the second end can be open to atmospheric pressure. In addition, the first end of the fluid conduit can be vertically lower than the second end when the bioreactor is assembled such that upon addition of a liquid to the conduit a pressure head is established in the conduit. In one embodiment, the conduit can have a cross-sectional area that is non-constant along the length of the conduit from the first end to the second end.

Also disclosed is a modular bioreactor. The modular bioreactor can include a first module and a second module. The first module includes a first compliance chamber. The first module is a removably attachable component of the modular bioreactor. The modular bioreactor can also include a second module that includes a second compliance chamber. The second module is also a removably attachable component of the modular bioreactor. More specifically, the second module is an alternative to the first module during assembly and use of the modular bioreactor. For instance, the first compliance chamber can include an end that is open to the atmosphere and the second compliance chamber can be a closed chamber that can operate above or below atmospheric pressure.

A method for conditioning a cellular material is also disclosed. For example, a method can include securing the cellular material in a bioreactor. The method can also include attaching a compliance chamber to the bioreactor, the compliance chamber being one of multiple alternative compliance chambers that are each removably attachable to the bioreactor. The method can also include establishing a pulsatile flow across the cellular material, the pulsatile flow being defined by characteristics including a stroke volume and a pressure differential that are at least partially established by the characteristics of the compliance chamber. The modular bioreactor can also include one or more reservoir modules that can be interchangeable with one another. In addition, the flow direction through the device can be reversed as desired. The modular bioreactor can provide a multi-functional system that can condition multiple different types of tissues.

BRIEF DESCRIPTION OF THE FIGURES

The present disclosure may be better understood with reference to the figures including:

FIG. 17A illustrates media and gas exchange processes for cell seeding chambers including the change of media without opening the lid by aspirating through a needleless port, FIG. 17B illustrates vacuum tubing connected to a port of a cell seeding chamber and FIG. 17C illustrates cycling of gas through the chambers via sterile filters and vacuum pressure.

FIG. 18 illustrates the top of a cell seeding chamber showing rotational markings.

Figure 1:
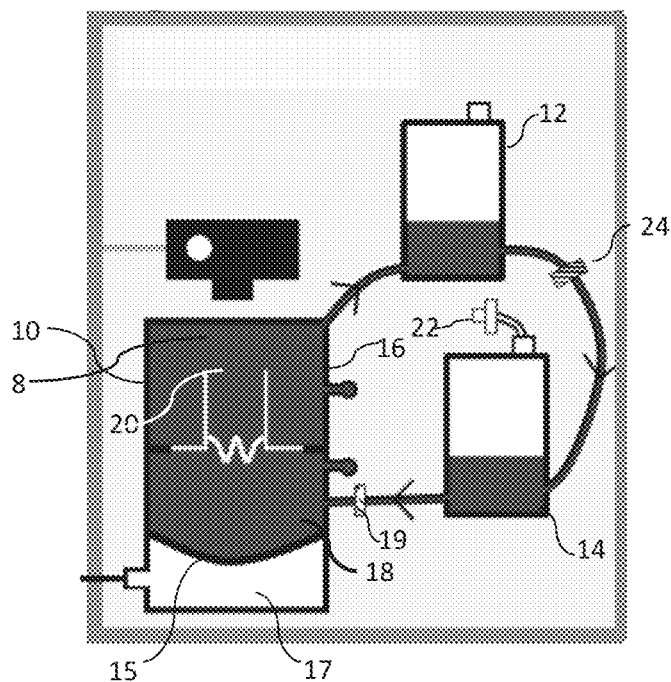
FIG. 1 presents a generalized version of a modular bioreactor as disclosed herein.

Repeat use of reference characters in the present specification and drawings is intended to represent the same or analogous features or elements of the present disclosure.

DETAILED DESCRIPTION

Reference will now be made in detail to various embodiments of the disclosure, one or more examples of which are illustrated in the accompanying drawings. Each example is provided by way of explanation of the subject matter, not limitation thereof. In fact, it will be apparent to those skilled in the art that various modifications and variations can be made in the present disclosure without departing from the scope or spirit of the subject matter. For instance, features illustrated or described as part of one embodiment, can be used on another embodiment to yield a still further embodiment.

The present disclosure relates generally to bioreactors and components of bioreactors for use in development and conditioning of cellular materials for study or implant. More specifically, disclosed are modular bioreactors and modular components of the bioreactors that can be easily assembled with alternative components to provide a predetermined conditioning environment for the cellular material (e.g., implantable tissue) with high specificity. For example, by selection of one of multiple alternative compliance chambers, a bioreactor can be utilized to condition tissue in a low pressure circuit (e.g., a pulmonary heart circuit), and by utilization of an alternative compliance chamber, the bioreactor can instead condition tissue in a high pressure circuit (e.g., an aortic heart circuit). The bioreactor can also be altered with regard to flow parameters, including flow direction, which can allow for use in conditioning a large variety of tissue types, e.g., mitral valves, aortic valves, pulmonary valves, etc.

As utilized herein, the term "tissue" generally refers to an organization of one or more components that can support and interact with living cells. A tissue can be a natural tissue obtained from a natural source (e.g., human or animal-derived tissue), and can include natural structural components such as the structural proteins collagen, elastin, laminin, etc. Alternatively, a tissue can be a synthetic tissue, in which the structural components can include synthetically formed materials, e.g., hydrogel networks and fibers, etc. that can include synthetic polymers. A synthetic tissue can also include natural polymers, such as collagen, alginates, etc., that have been processed in some fashion to form the synthetic tissue. The cells supported on/in a tissue can be the cells that are naturally present in a natural tissue or can be cells that are seeded on the natural or synthetic tissue for study and/or implantation in a living subject. The term "tissue" can refer to both the acellular structural scaffolding material as well as the scaffolding material in conjunction with cells.

As utilized herein, the term "cellular material" generally refers to any material that includes living cells for placement in a bioreactor. For instance, a cellular material can include cells held on or in a matrix that can be formed of either natural or synthetic materials. The cellular material can be a tissue or can be any other material that contains living cells. For example, cellular material as may be conditioned by use of a bioreactor can include a plurality of cells held within an enclosure or otherwise contained, though not necessarily on or in an implantable scaffolding material.

While the bioreactor can be utilized in one particular embodiment for use with vascular cellular material, this is not a requirement of the bioreactors and components therefor as disclosed herein. For instance, while the bioreactors and components therefor are particularly well suited for use with cardiac implants (e.g., cell-seeded or acellular bioprosthetic, tissue engineered, or mechanical heart valves), the use of the devices described herein is in no way limited to such materials. Beneficially, the cell seeding apparatus, compliance chambers, and modular bioreactors described herein can be utilized with any tissue or cellular material in any pulsatile flow environment.

Generally speaking, a modular bioreactor can include two or more modules that are removably attachable to one another and that, upon attachment, can secure a cellular material (e.g., a tissue or other cellular material) within the bioreactor such that during use the cellular material can be subjected to a pulsatile shear stress due to flow of a liquid through and/or across the surface of the cellular material. Methods and devices for attaching the modules to one another can include fittings as are generally known in the art. By way of example, fittings as described in U.S. Published Patent Application No. 2013/0341916 to Sierad, et al. may be utilized. For example, one of the components can be a compliance chamber and the flow through the bioreactor can be a pulsatile flow that can mimic flow characteristics found in vivo, for instance, in the heart.

FIG. 1 illustrates one generalized schematic of a modular bioreactor. In this embodiment, the modular bioreactor can include a first module 10, a second module that includes a compliance chamber 12, and a third module that includes a reservoir 14, The first module 10 can include a holder 8 that can secure a cellular material 20 to be conditioned within the bioreactor. For instance, the holder 8 can be located between an upper chamber 16 and a lower chamber 18 of the first module 10. As liquid flows through the bioreactor (as designated by the directional arrows), the liquid (dark in FIG. 1) will flow past the cellular material 20 secured in the holder 8. The first module 10 also includes a pressure chamber 17 that can be in fluid communication with a pressurized fluid source (e g, high pressure air) that can be separated from the liquid in the lower chamber 18 by a flexible membrane 15. Upon an influx or outflow of pressurized fluid to/from the pressure chamber 17, the flexible membrane 15 can distend into the lower chamber 18 or retract into the pressure chamber 17, and drive fluid flow through the bioreactor. In other embodiments discussed in more detail herein, the individual chambers of a module can, in turn, be separable modules that can be removably attachable to one another.

Reservoir 14 can provide for gas exchange by use of a suitable gas exchange filter 22 and can also be utilized to control flow characteristics such as turbidity through the system. For instance, through control of the liquid volume held in the reservoir, the turbidity of the flow across the cellular material 20 held in the module 10 can be controlled.

The bioreactor of FIG. 1 also includes a compliance chamber 12. The use of a compliance chamber in circulatory loop construction is known in simulation of arterial or venous flow. Development of a circulatory loop for a bioreactor in cardiac assist technologies as well as other pulsatile flow technologies necessitates that the bioreactor should be capable of reproducing the circulatory conditions that exist physiologically. The compliance chambers as described herein can provide this capability through use of improved compliance chambers that can facilitate the simultaneous simulation of both the physiological pressures and stroke volumes of a pulsatile flow, which has been difficult or not attainable previously. The compliance chambers as described herein can also provide this capability through the use of alternative modular compliance chambers that can be interchanged to quickly and easily simulate a wide range of pulsatile flow conditions.

Figure 2A:
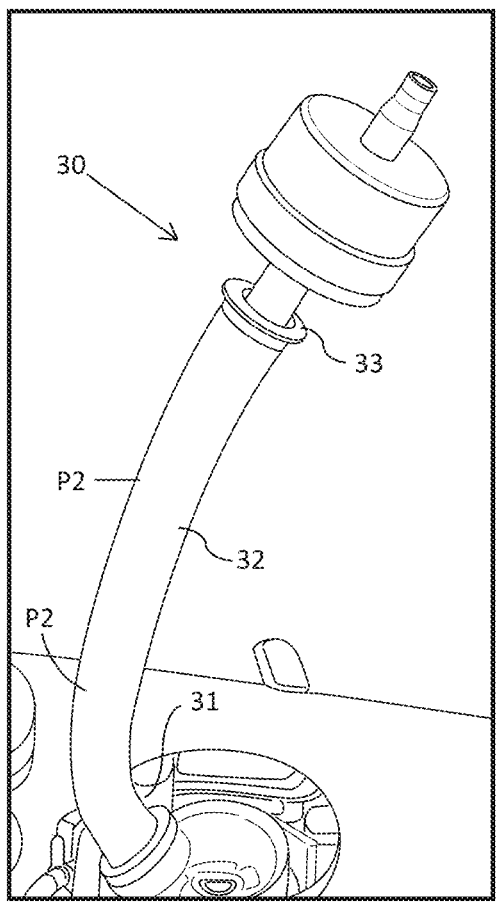
FIG. 2A illustrates a first embodiment.
Figure 2B:
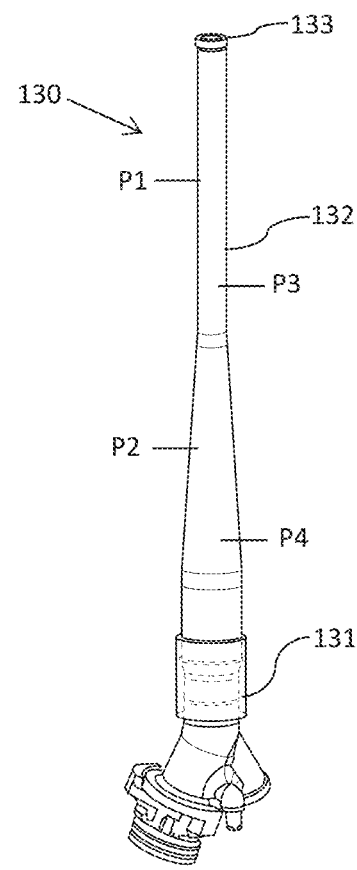
FIG. 2B illustrates a second embodiment of open-ended compliance chambers as may be utilized as alternative components of a modular bioreactor.

FIG. 2A illustrates one embodiment of an open-topped compliance chamber 30 as may be a component of a bioreactor as disclosed herein. Open-topped compliance chamber embodiments of which are illustrated in FIG. 2A and FIG. 2B may be particularly useful for examining a low pressure pulsatile flow, such as a venous flow generally or flow through the right side of the heart. For instance, an open-topped compliance chamber can be utilized to establish a pulsatile flow with a total pressure differential over a single pulse cycle from about 2 mmHg to about 40 mmHg, or from about 5 mmHg to about 20 mmHg, in some embodiments. In addition, the upper pressure for an individual pulse cycle of a flow (e.g., a systolic pressure) can be from about 10 mmHg to about 45 mmHg and the lower pressure of an individual pulse cycle of a flow (e.g., diastolic pressure) can be from about 5 mmHg to about 30 mmHg. The stroke volume of a single pulse cycle in a bioreactor utilizing an open-topped compliance chamber can be from about 10 mL to about 200 mL, or from about 50 mL to about 90 mL, or from about 60 mL to about 80 mL, in some embodiments. For instance, the stroke volume can be similar to a typical heart stroke volume of about 70 mL.

As can be seen, the compliance chamber 30 includes a conduit 32 that extends from a first end 31 to a second end 33. The conduit 32 can generally have a length of about 2 inches or greater. The conduit 32 can be formed of any suitable material including, for instance, glass or a polymeric material. In one embodiment, the conduit can be formed of a transparent material to allow for examination of the fluid within the conduit 32 during use.

The first end 31 of the conduit 32 can be in fluid communication with the liquid flow through the remainder of the bioreactor to allow for a column of the circulating liquid to be established within the conduit 32. The second end 33 of the conduit 32 can be at atmospheric pressure. While the second end 33 of the conduit can be simply open to the atmosphere, in general, the second end 33 can include an air filter 35 to prevent contamination of the system while still maintaining an open communication to hold the second end 33 of the conduit 32 at atmospheric pressure.

The height of the liquid column within the conduit 32 will develop a pressure head on the liquid circulating through the system. In addition, the pulsatile flow through the system (developed by use of a pulsing input pressure to the bioreactor, described further herein), will vary the column height over the course of a single pulse from a high pressure head (one example of which is marked as $p_1$ on FIG. 2A) to a low pressure head (exemplary marked as $p_2$ on FIG. 2A). This difference in height ($p_1$-$p_2$) can establish the pressure differential over the course of a single pulse in the flow. In addition, the pressure head at $p_1$ and the pressure head at $p_2$ can be utilized to establish the upper and lower pressures (e.g., systolic and diastolic pressures) of a single pulse.

FIG. 2B illustrates another embodiment of an open-topped compliance chamber 130. As can be seen, the conduit 132 of compliance chamber varies in diameter from the first end 131 of the conduit to the second end 133 of the conduit. The compliance chamber 130 can utilize the variable conduit 132 in control of stroke volume of a single pulse. Specifically, the difference in liquid volume in the conduit 132 between $p_1$ and $p_2$ can correspond to the stroke volume of a single pulse. However, as the conduit 132 defines a variable cross sectional area along the axial length of the conduit from the first end 131 to the second end 133, the volume of fluid held in any single section can vary from that of a different section. For example, when considering a conduit 132 that is circular in cross section (though the cross sectional geometry of a conduit is in no way limited to a circular cross section), the diameter of the cross section can decrease from the first end 131 to the second end 133. For instance, the diameter at the larger end 131 of the conduit can be from about 0.25 inches to about 2 inches in one embodiment and the diameter at the smaller end 133 can be from about 0.1 inches to about 1.5 inches in one embodiment. By varying the specific location of $p_1$ and $p_2$ along the length of the conduit 132 to $p_3$ and $p_4$, but maintaining the differential pressure across the pulse ($p_1$-$p_2$)=($p_4$-$p_3$), the stroke volume and maximum and minimum pressures can be varied, while the differential pressure $\Delta p = (p_1-p_2) = (p_4-p_3)$ can remain the same over a pulse. In addition, by substituting a different open topped compliance chamber that is the same except for the diameter of the conduit and maintaining the location of $p_1$ and $p_2$ by varying the pulsed input pressures, the upper and lower pressures over the course of a pulse cycle can remain the same, and the stroke volume can be varied. A variation in stroke volume while maintaining pressure characteristics can thus be obtained by varying the geometry of the conduit, either by replacing the conduit (e.g., utilizing a different compliance chamber module) or by altering the geometry of the existing conduit (e.g., by clamping, compressing the conduit to vary the volume between $p_1$ and $p_2$).

The additional inclusion in the system of a pressure control valve in conjunction with the compliance chamber can provide additional control mechanisms to the system. For instance, and with reference to FIG. 1, the inclusion of a constriction valve 24 downstream of the compliance chamber 12 can provide additional control schemes to the pressure characteristics and stroke volume of individual pulses of the pulsatile flow. By way of example, upon establishment of a desired stroke volume and the associated location of the upper and lower end of the stroke during a pulse to achieve the desired upper and lower pressures (i.e., the location of $p_1$ and $p_2$ for the desired stroke volume and pressures while using a conduit of specific change in cross sectional area), the desired stroke volume and pressure values can be further altered by variation in the characteristics of a downstream (or upstream, depending upon the direction of flow) constriction valve. Constriction valves as are generally known in the art can be utilized in a bioreactor such those described, for example, in U.S. Published Patent Application No. 2012/0298891 to Matthiesen, which is incorporated herein by reference.

Figure 3:
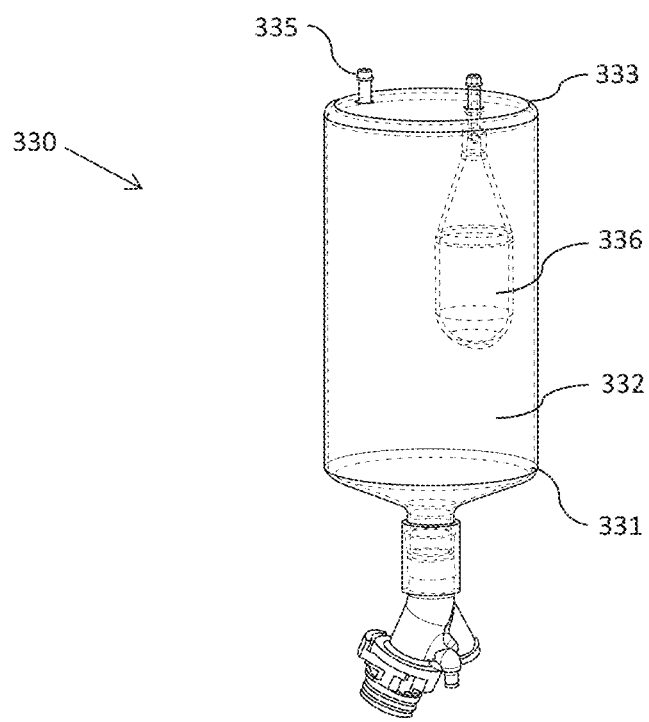
FIG. 3 illustrates a sealed compliance chamber as may be utilized as a component of a modular bioreactor.

FIG. 3 illustrates an alternative compliance chamber 330 that can be utilized in a modular bioreactor. Compliance chamber 330 can generally be utilized for higher pressure flow characteristics as compared to compliance chamber 30 of FIG. 2A or compliance chamber 130 of FIG. 2B. For example, a sealed compliance chamber such as compliance chamber 330 can be utilized for a pulsatile flow having a pressure differential over a single pulse cycle of from about 10 mmHg to about 150 mmHg, from about 20 mmHg to about 100 mmHg, or from about 30 mmHg to about 50 mmHg, in one embodiment. The higher pressure (e.g., a systolic pressure) of a single pulse cycle using compliance chamber 330 can be, for example, from about 70 mmHg to about 250 mmHg, or from about 100 mmHg to about 140 mmHg, in some embodiments. The lower pressure (e.g., a diastolic pressure) of a single pulse cycle using compliance chamber 330 can be, for example, from about 30 mmHg to about 150 mmHg, or from about 55 mmHg to about 95 mmHg, in some embodiments.

Compliance chamber 330 includes a sealed rigid container 332 that is sealed from the surrounding atmosphere. The first end 331 of the rigid container 332 can be in fluid communication with the liquid flow through the bioreactor to allow for an amount of the circulating liquid to be established within the rigid container 332. The second end 333 of the sealed rigid container 332 can be in fluid communication with a gas source as at 335 that can feed a pressurized gas to sealed container 332. The rigid container of a compliance chamber can be of any size, for instance from about 0.1 liter to about 10 liters in some embodiments, or from about 1 liter to about 2.5 liters in some embodiments, though larger or smaller rigid containers can optionally be utilized.

Through establishment of a counter pressure via the pressurized gas held in the rigid container 332, a pressure differential as well as the high and low pressures of a single pulse can be established. A constriction valve located upstream or downstream of the compliance chamber 330 can also be used in conjunction with the compliance chamber 330 as discussed above with regard to open-topped compliance chambers. Sealed compliance chamber 330 is similar to pressurized compliance chambers utilized in previously known pulsatile flow bioreactors, but can be operated with variance in the pressure, liquid volume, and initial air volume in the compliance chamber. As such, the compliance chamber 330 can be utilized in a bioreactor system that can have a variable stroke volume and pressure characteristics through variation in the liquid volume as discussed above with regard to the open-topped compliance chambers as well as through variation in the gas pressure and gas volume of the compliance chamber 330.

The stroke volume of a single pulse when using a sealed compliance chamber as illustrated in FIG. 3 can also be varied. For instance, at a given set of pressure conditions, the stroke volume can be altered by variance of the volume of the gas within the rigid container, e.g., by utilization of a different modular compliance chamber that has a sealed rigid container of a different volume, by using a rigid container that has a variable cross sectional area over the length of the container, as described above for the compliance chamber 130, or by adding or removing air inside the rigid container without changing the container itself, which can be done in the course of a conditioning operation. This latter alternative would simultaneously alter the total volume of liquid in the system, i.e., the volume of liquid that is subject to the pressurized gas within the rigid container 132. In another embodiment, the rigid container 132 can incorporate an inner chamber 336 that can be filled with an incompressible fluid such as water and the inner chamber 336 can be pliable such that the inner chamber 336 can expand upon addition of the fluid and can contract upon removal of the fluid. In one embodiment, the inner chamber 336 can be in fluid communication with a source of an incompressible fluid and the volume of the inner chamber 336 can be varied prior to or during operation of the bioreactor. Thus, the characteristics of the operation of the bioreactor can be varied during conditioning of the cellular materials without stopping the pulsatile flow through the bioreactor.

Figure 4:
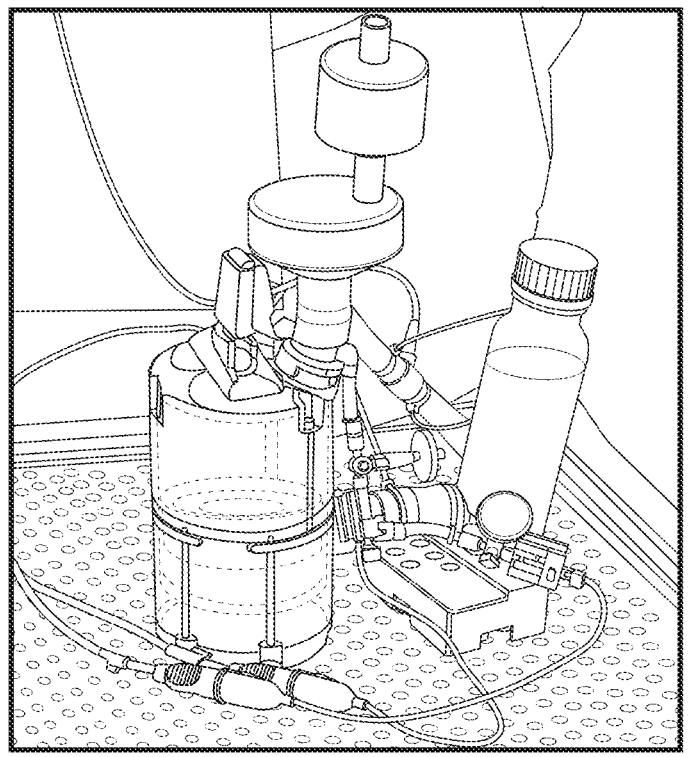
FIG. 4 illustrates a modular bioreactor in a mitral valve simulation set up.

Through use of one of the alternative compliance chambers in a bioreactor system, a wider range of physiological conditions can be established with a modular system. For instance, the bioreactor system can alternatively be utilized to simulate high pressure flow on the left side of the heart through use of a compliance chamber 330 as illustrated in FIG. 3 or to simulate low pressure flow on the right side of the heart through use of a compliance chamber 30 or 130 as illustrated in FIG. 2A and FIG. 2B. Direction of flow through the bioreactor can be in either direction, which can also be utilized to alter the conditions of a particular protocol. For instance, as illustrated in FIG. 4, a modular bioreactor is set up to synthesize mital valve flow. In this embodiment, flow through the device will be in the opposite direction as for other valve types, such as atrial valve simulations.

Figure 5:
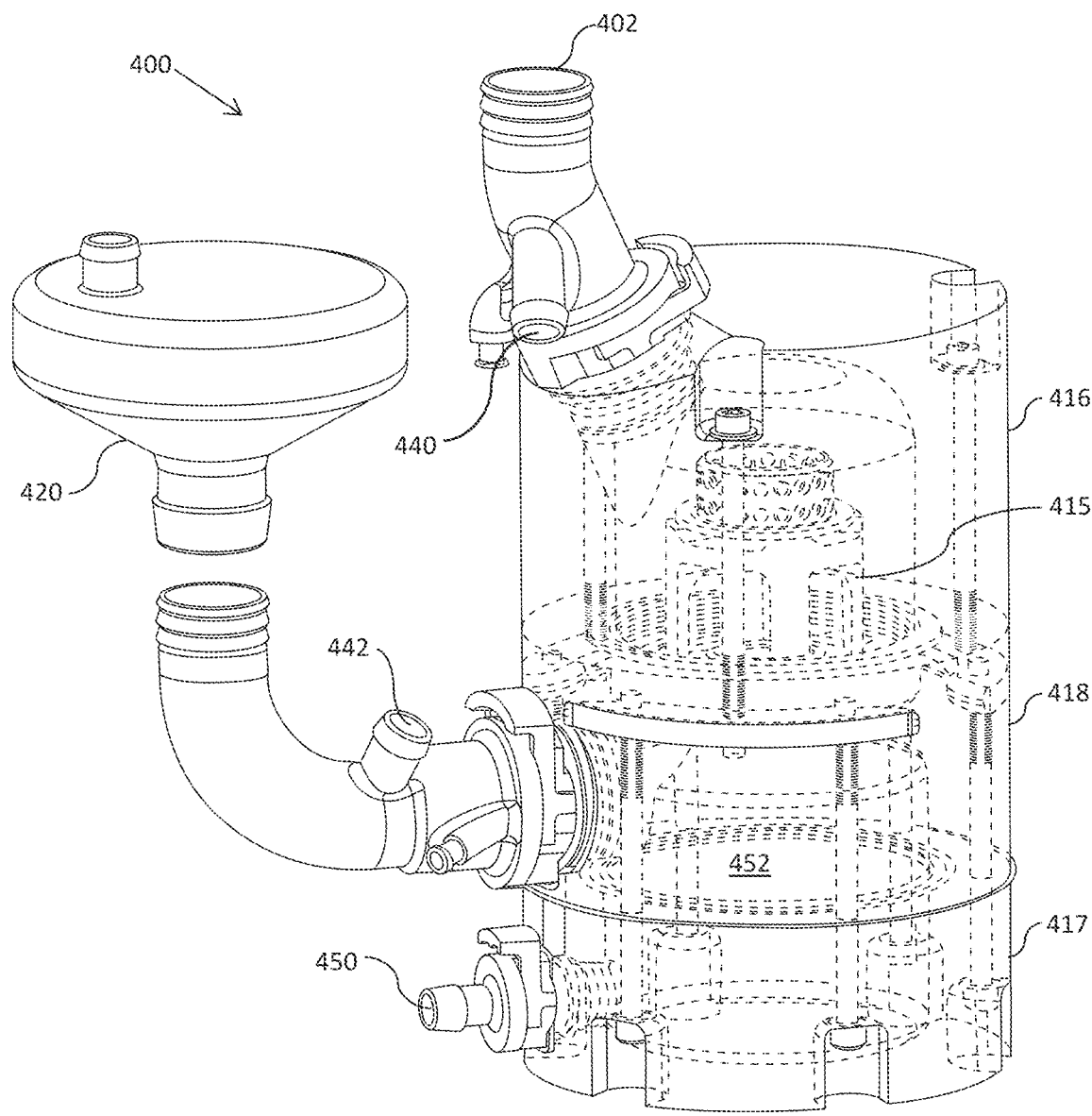
FIG. 5 illustrates one embodiment of a modular bioreactor.

FIG. 5 illustrates a modular bioreactor 400 that can be utilized in conjunction with any one of alternative compliance chambers such as, for example, one of the compliance chamber 30, the compliance chamber 130, or the compliance chamber 330 discussed above. Modular bioreactor 400 includes a pressure module 417, a first conditioning module 418, a second conditioning module 416, and a reservoir module 420. In this illustration, the bioreactor 400 is not connected to a compliance chamber. When fully assembled, a compliance chamber could be attached to the bioreactor at attachment 402. Access 440 provides a route for flow to or from reservoir module 420 via access 442.

Figure 6A:
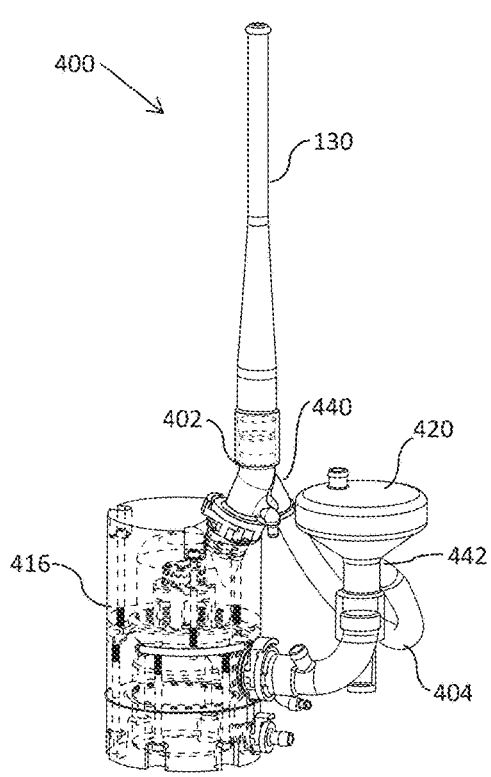
FIG. 6A illustrates the modular bioreactor of FIG. 5 assembled with the compliance chamber of FIG. 2B.

For example, FIG. 6A illustrates the bioreactor 400 following assembly with the open-topped compliance chamber 130 attached in fluid communication between the second conditioning module 416 and the reservoir module 420. The flow line 404 connects the outlet 440 of the compliance chamber 132 and the inlet 442 of the reservoir 420.

Figure 6B:
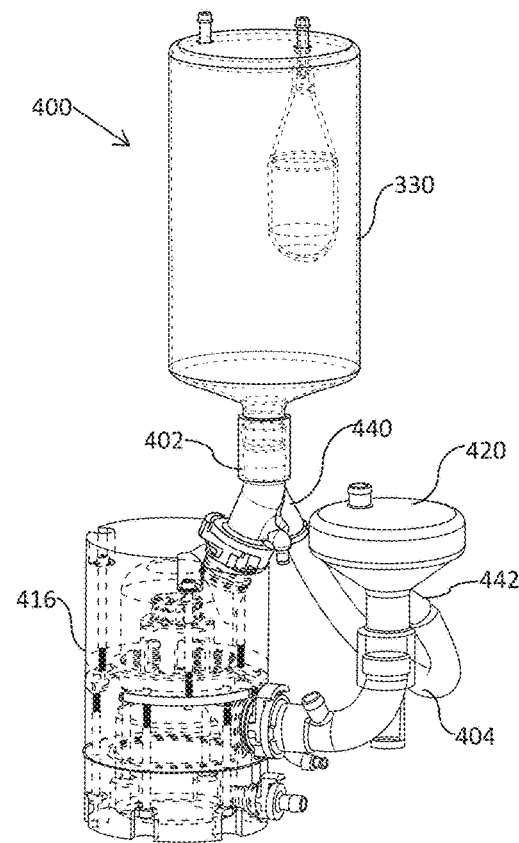
FIG. 6B illustrates the modular bioreactor of FIG. 5 assembled with the compliance chamber of FIG. 3.

In an alternative embodiment of the modular bioreactor, FIG. 6B illustrates the bioreactor 400 following assembly with the sealed compliance chamber 330 attached in fluid communication between the second conditioning module 416 and the reservoir module 420. The assembly is the same other than the utilization of the alternative compliance chamber, with a flow line 404 providing fluid communication between the outlet 440 and the inlet 442. As stated, the flow line 404 can optionally include a constriction valve (not illustrated in FIG. 6A or FIG. 6B), flow meter, etc. as are known in the art that can provide further control mechanisms to the bioreactor.

Referring again to FIG. 5, the bioreactor 400 can include a holder 415 that can hold cellular material (e.g., tissue) for conditioning in the bioreactor. Though illustrated primarily within the interior of conditioning module 416, this is not a requirement of a bioreactor, and the holder can be within the first conditioning module 418, the second conditioning module 416, or alternatively in a flow path between the two. For instance, in the mitral valve set up shown in FIG. 4, the holder is primarily in the lower conditioning module of the bioreactor.

The individual modules can be formed of the same materials as one another or different materials, as desired. For example, the modules can be formed of glass, ceramic, polymeric materials, or the like. In one embodiment, at least the conditioning modules 416, 418 can be transparent, which can allow for visual assessment of the cellular material held inside during a conditioning operation. For instance, the conditioning modules 416, 418 can be transparent acrylic or glass.

Figure 7:
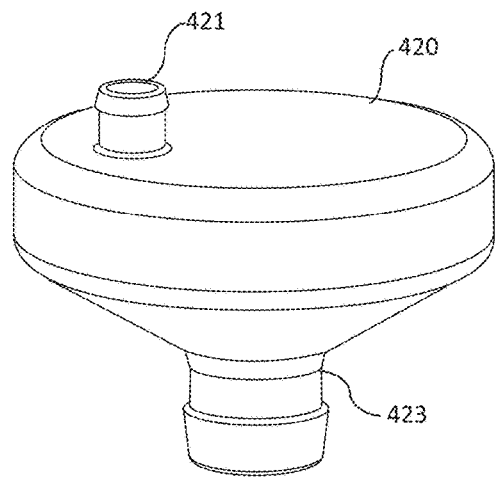
FIG. 7 illustrates a reservoir module of a modular bioreactor.

A reservoir module is illustrated in FIG. 7. As shown, the reservoir module 420 can include a vent 421 that can provide for gas exchange with the liquid carried through the bioreactor. The size, shape and configuration of the reservoir 420 with respect to the other components of the bioreactor can all be varied according to standard practice to affect flow characteristics through the bioreactor. For instance, the vertical distance from the inlet 442 (FIG. 5) to the base 423 of the reservoir 420 can be varied, with a longer vertical distance (i.e., high pressure head) decreasing overall flow through the system. Alternatively, a shorter distance can decrease turbulence of the flow downstream of the reservoir 420 as well as increase fluid movement within the reservoir 420 to provide an increased gas exchange. Thus, a bioreactor system can include multiple reservoir modules that can be alternatively utilized to vary flow characteristics of a conditioning process.

Figure 8:
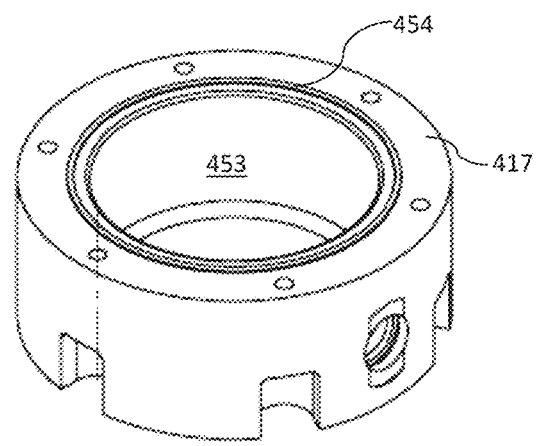
FIG. 8 illustrates a pressure module of a modular bioreactor.

FIG. 8 illustrates a pressure module 417 for a modular bioreactor. The pressure module 417 can include a pressure inlet 450 that can be in fluid communication with a pressurized gas source (e.g., air). The pressure module 417 can be assembled with the other modules so as to transfer a pulsatile pressure from the pressurized gas source to the liquid carried in the bioreactor and thereby drive the pulsatile flow through the bioreactor. For instance, in the illustrated embodiment a flexible membrane 452 (FIG. 5) can be attached between the pressure module 417 and the first conditioning module 418. The membrane can seal the access 453 on a portion of the pressure module 417 and can be, for example, a semi-permeable or impermeable membrane that upon the applied pressure from the pressurized gas source can distend or retract and drive flow through the system. For example, the flexible membrane 452 can be a silicone membrane as is known in the art attached in a retaining ring 454 at opening 453. High pressure gas can then be pulsed into the pressure module 417 via inlet 450 to periodically distend or retract the flexible membrane 452 and drive flow through the bioreactor.

Figure 9A:
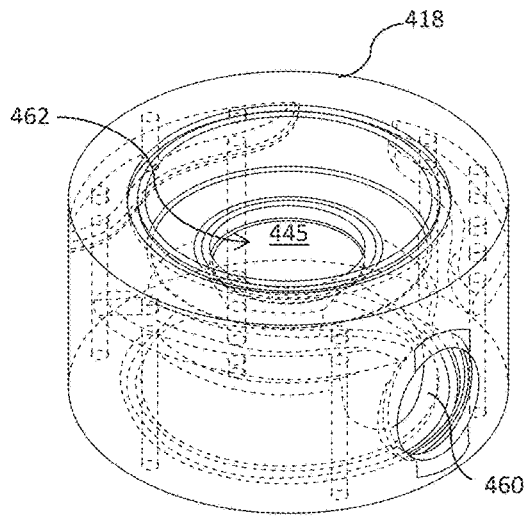
FIG. 9A illustrates a perspective view.
Figure 9B:
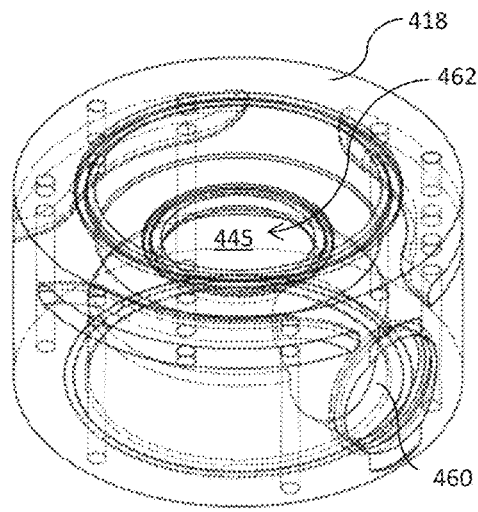
FIG. 9B illustrates a transparent perspective view with external shading removed of a first conditioning module of a modular bioreactor.

One embodiment of the first conditioning module 418 is illustrated including a perspective view (FIG. 9A) and a transparent perspective view (FIG. 9B) that better illustrates the internal design of the first conditioning module 418. As can be seen, the first conditioning module 418 can include an access 460 to the conditioning chamber 462 within the module 418. During use, flow can pass through the access 460 to or from the chamber 462.

As previously stated, the bioreactor can be operated with flow in either direction, i.e., circulating from the first conditioning module 418 to the second conditioning module 416 past one of the alternative compliance chambers and the reservoir module 420 to return to the first conditioning module 418 via the access 460 or alternatively in the opposite direction. To ensure that the pressure module 417 drives flow in the desired direction, the bioreactor can also include a one-way valve (FIG. 1, 19), for instance at the access 460, that can be reversed to direct flow in the desired direction.

Figure 10A:
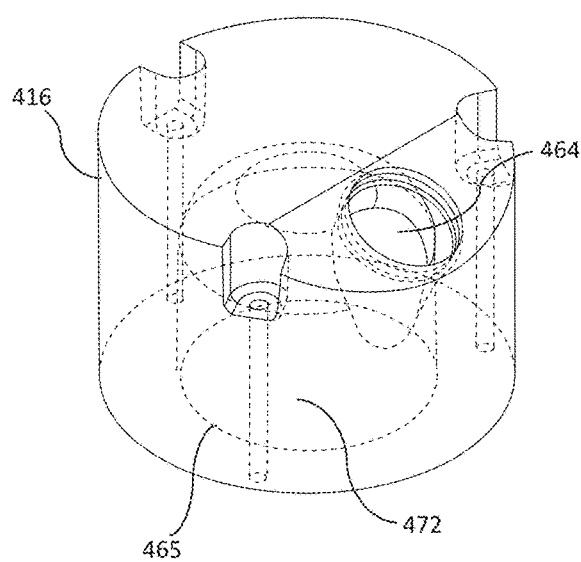
FIG. 10A illustrates a perspective view.
Figure 10B:
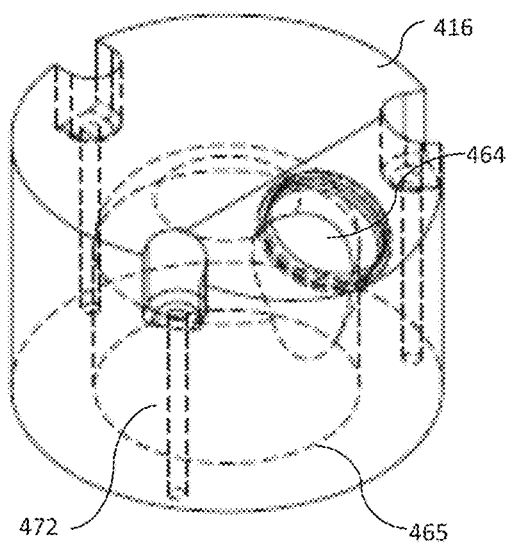
FIG. 10B illustrates a transparent perspective view with external shading removed of a second conditioning module of a modular bioreactor.

Module 418 also includes an access 445 to the conditioning chamber 462 that allows fluid communication between the conditioning chamber 462 of conditioning module 418 and a conditioning chamber 472 of conditioning module 416 (FIG. 10A, FIG. 10B).

The second conditioning module 416 is illustrated in a perspective view (FIG. 10A) and in a transparent perspective view (FIG. 10B) that better illustrates the internal design of the second conditioning module 416. The second conditioning module 416 includes an access 464 that provides a flow path for fluid passing out of the conditioning chamber 472 of the second conditioning module 416. The second conditioning module 416 also includes an access 465 to the conditioning chamber 472 of the second conditioning module 416.

During assembly, access 445 of the first conditioning module 418 can be aligned with access 465 of the second conditioning module 416 such that liquid can be communicated between the conditioning chambers 462, 472 of the two conditioning modules 418, 416 during use. During operation, cellular material can be held within one or both of the conditioning chambers 462, 472 and/or in a flow path that can be established between the two conditioning chambers 462, 472 (e.g., at the meeting point of access 445 and access 465) during use of the bioreactor.

Figure 11:
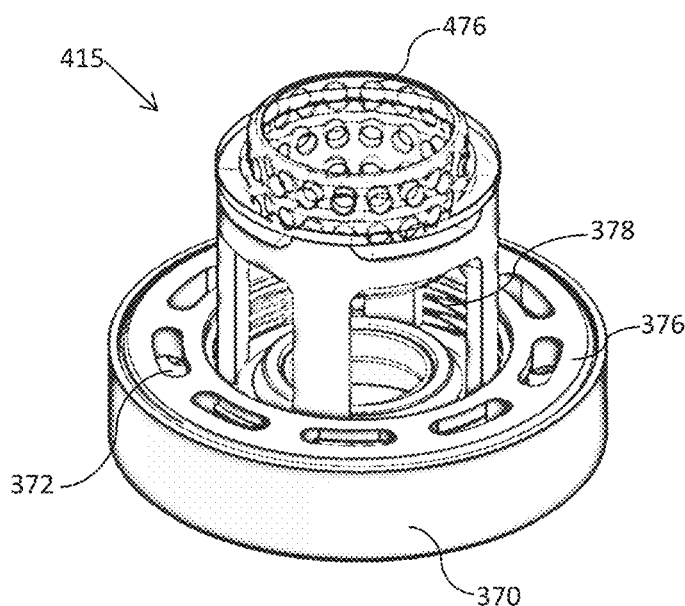
FIG. 11 schematically illustrates a tissue holder that may be utilized in conjunction with a modular bioreactor.
Figure 12:
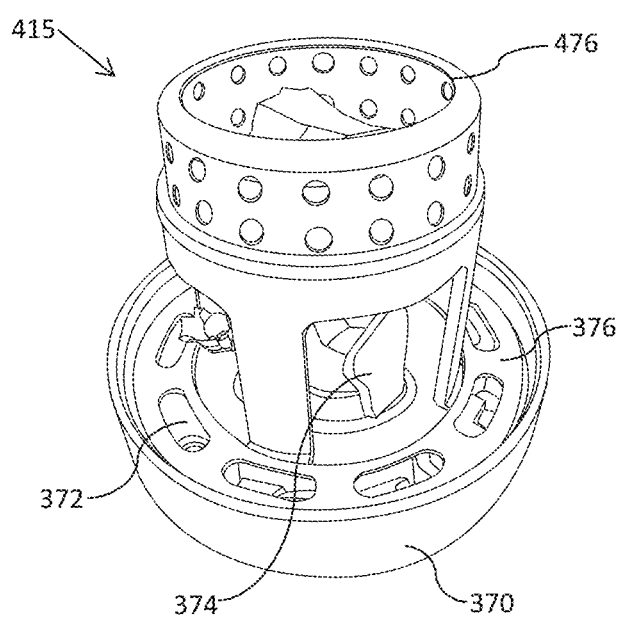
FIG. 12 is a photograph of a tissue holder as in FIG. 11 securing a heart valve tissue.

In general, the cellular material to be conditioned by use of the bioreactor can be secured by use of a holder. For instance, a tissue sample can be secured by a holder 415 as illustrated in FIG. 11 and FIG. 12. Tissue holder 415 is a self-adjusting tissue holder that can be removably located within the access 445 of conditioning module 418. It should be understood, however, that any cellular material holder can be utilized with the bioreactor system, and the utilization of tissue holder 415 is not a requirement, but merely one embodiment of a cellular material holder for use with the bioreactor.

Briefly, the self-adjusting tissue holder 415 includes a first holding plate 370 and a second holding plate 372 that are aligned with one another and hold a portion of the tissue segment 374 there between. The self-adjusting tissue holder 415 also includes a clamping mechanism 376 that, when tightened and attached to the first holding plate 370 at the side wall of the first holding plate 370, can press a spring 378 against the second holding plate 372. The spring 378 can maintain pressure between the two plates 370, 372 and secure the portion of the tissue segment 374 that is held between the two holding plates 370, 372 so as to prevent leakage around the tissue segment or release of the tissue segment from the tissue holder 415.

The tissue segment 374 pictured in FIG. 12 is a heart valve tissue segment that can include the vessel wall and sinus, which can be seen in FIG. 12 within a support structure 476 of the holder 415. The heart valve tissue segment 374 can also include a valve, the cusps of which are within the lumen of the tissue segment 374 and not visible in FIG. 12. The heart valve segment 374 can also include muscle tissue, which may be on the external portion of the segment and/or may be on the internal tissue wall. During conditioning of the tissue segment 374, the tissue segment 374 can be held within one or both of the conditioning chambers 462, 472 such that the tissue is subjected to the pulsatile flow through the bioreactor.

Figure 13:
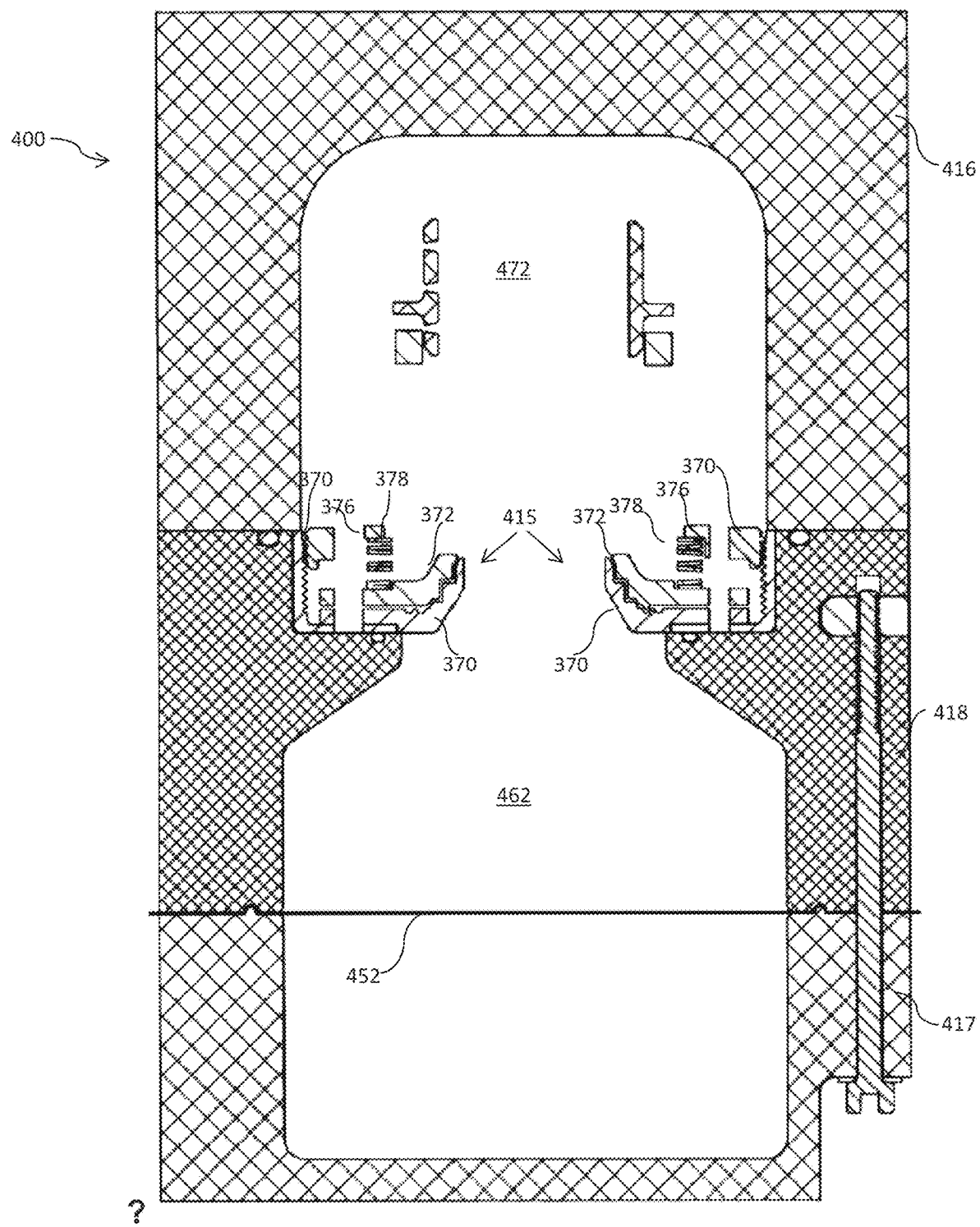
FIG. 13 illustrates a sectional view of a first conditioning module, a second conditioning module, a pressure module, and a tissue holder assembled together.

FIG. 13 is a sectional view of a bioreactor 400 including the pressure module 417, the first conditioning module 418, the second conditioning module 416 and a tissue holder 415 secured at the junction of the first and second conditioning modules 418, 416. As illustrated and discussed above, the bioreactor 400 includes a flexible membrane 452 between the pressure module 417 and the first conditioning module 418.

The tissue holder 415 includes the first holding plate 370 and the second holding plate 372 that can be held tightly together by use of the spring 378 and the clamping mechanism 376. Specifically, the clamping mechanism 376 is in a threaded arrangement with the side wall of the first holding plate 370 holding the spring 378 against the second holding plate 372 to secure a tissue portion (not shown in FIG. 13) between the two holding plates 370, 372 such that another portion of the tissue can be subjected to flow between the conditioning chamber 462 of the first conditioning module 418 and the conditioning chamber 472 of the second conditioning module 416.

A bioreactor can be utilized to condition any cellular material. By way of example, in one embodiment, a bioreactor can be utilized to examine the effect of an active agent on a natural tissue, for instance in a new drug testing application. For example, a natural tissue can be secured in a system, and the liquid pulsatile flow can carry a biologically active agent. The testing protocol can then examine the results of the interaction of the biologically active agent on the natural tissue under the physiological flow conditions that can be established within the bioreactor.

In another embodiment, the bioreactor can be utilized to condition a supporting scaffolding material that naturally contains and/or has been seeded with cells. For instance, the bioreactor can be utilized for growth and development of a three dimensional cellular construct, such as in tissue engineered replacement therapy. In this embodiment, a scaffold, for instance a biodegradable natural or synthetic scaffold seeded with stem cells, can be conditioned in the bioreactor as the cells grow and develop a replacement tissue for implantation. The replacement tissue including a support structure can develop as the scaffolding material degrades and is replaced by the natural material of the cellular construct. By development under progressively increasing flow conditions, the engineered tissue is much more likely to survive and continue to develop in a sustainable, natural fashion following implantation.

In another embodiment, a nondegradable scaffolding material can be utilized (e.g., a mechanical heart valve or a nondegradable scaffolding material based on synthetic and/or natural structural polymers) and the cells seeded on the scaffolding can be conditioned within the bioreactor prior to implant, which can encourage long term attachment of the cells at the surface of the nondegradable scaffolding material.

Prior to seeding cells onto a natural scaffolding material, the natural material can be decellularized. Decellularization can be carried out according to any suitable fashion such as via immersion as is generally known in the art. In one embodiment, a natural scaffold (e.g., a xenograft implant) that includes a lumen and a tissue wall can be decellularized by use of a pressurized decellularization technique as disclosed in a co-owned patent application. Briefly, a natural tubular scaffold such as a vessel segment (e.g., a vessel segment including a heart valve) can be secured at each end and within a decellularization chamber such that a first flow path is established that passes through the lumen of the tissue segment and contacts the interior surface of the tissue wall and a second flow path is established that contacts the exterior surface the tissue wall. The system can also include a pump that can pump a decellularization solution through the first path and establish a pressure differential across the tissue wall. The pressure differential can encourage decellularization of the tissue wall. In one embodiment, the pressure differential can be pulsed.

A decellularized (and in one embodiment acellular) scaffold can then be reseeded and conditioned by use of a modular bioreactor as disclosed herein. Combining a natural but decellularized scaffold with desired reseeded cells, such as, for instance, a patient's own stem cells, followed by conditioning in the modular bioreactor can provide a cellularized tissue that is fully functional for study or implant. An implanted tissue that is preconditioned by the disclosed bioreactor can be fully functional from initial implantation and able to maintain matrix homeostasis and reduce thrombogenicity for the long term, e.g., the lifetime of the patient.

According to one embodiment, a natural or synthetic scaffold can be seeded during conditioning of the tissue within the bioreactor. In this embodiment, the liquid that is pulsed through the bioreactor can contain the desired cells and the cells can adhere to the tissue during the conditioning process.

Figure 14:
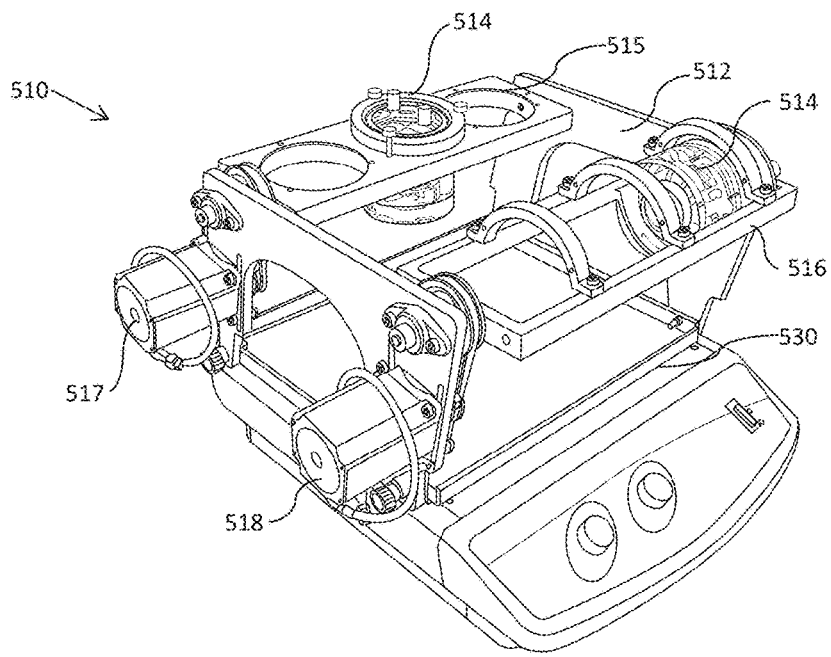
FIG. 14 illustrates a cell seeding apparatus.

In another embodiment, the scaffold can be seeded prior to conditioning by use of a rotational cell seeding apparatus, one embodiment of which is illustrated in FIG. 14. The cell seeding apparatus 510 can include a frame 512 that can include one or more rotatable plates 515, 516, each of which being capable of holding one or more seeding chamber 514 during a cell seeding operation. As can be seen, the rotatable plates 515, 516 need not hold the seeding chambers in the same orientation. For instance, a first rotatable plate 515 holds the cell seeding chamber 514 in an upright orientation and a second rotatable plate 516 holds the cell seeding chamber 514 in a sideways orientation.

Cell seeding chambers (FIG. 17A) can be utilized with very little seeding solution, which can reduce violent flow patterns that could cause cell removal from the scaffold or cell death. Rounded edges that fit closely to the outline of the tissue, e.g., an aortic root, can be designed with dimensions that can cause the fluid to flow smoothly through the slits in the mounting device as well as the tissue itself. The lid of the chamber can include multiple ports (FIG. 17B) that can provide a site for pressure equalization and media or gas exchange as necessary. During end-over-end rotation, for example, needleless ports can be added to luer ports, and during axial rotation, luer plugs can be used which can better fit the chambers into a holder plate, of course, variations in the geometry and port styles can be carried out depending upon the specifics of a system. O-ring seals and the like can be used to maintain sterility and slides in known fashion. The chamber and lid can be formed of any suitable material, such as an acrylic material that can allow visualization of flow and sterilization via ethylene oxide-gas treatment.

Multiple seeding chambers can be mounted into a holder plate (FIG. 17C). The holder can be mounted onto a frame containing a stepper-motor that can provide rotation of the holders. In one embodiment, a frame can be designed to hold multiple holder plates, which can provide for the processing of multiple tissue samples at one time. The frame can be mounted onto an orbital shaker that can provide an additional direction of motion to help maintain suspension of the cells and create random fluid movement within the chamber (FIG. 14). The entire assembly of chambers, holders, frames, motors, and orbital shaker can fit into a standard cell culture incubator or heating oven to provide physiological temperature during seeding.

A system can include multiple versions of chamber holder plates that can be exchanged. For example, a first holder plate can hold the seeding chambers so they rotate in an end-over-end fashion around the point directly in the center of each tissue sample (FIG. 14—upper plate) while a second chamber holder can hold the seeding chambers so they rotate around their natural axis (FIG. 14—lower plate). The different rotations can provide complete cell seeding. For instance, when considering cell seeding on a heart valve root, the end-over-end rotation and pauses at specific orientations can ensure that cells flow through a valve scaffold and contact multiple areas of a valve when they fall due to gravitational forces during the static phases. The axially rotating chamber holder can ensure cell contact with all interior surfaces of a valve root and may provide additional coverage over the alternative chamber holder.

Marking systems (FIG. 18) can be used to ensure uniform conditions between tissue samples and track areas already seeded with cells when performing multiple seeding steps. For example, each seeding chamber and lid set can be labeled with a unique number to identify and track each tissue sample. The seeding chambers can also be marked between each connection to the holder (e.g., each bolt) with degree marks (e.g., 0, 120, and 240). Using such marks, and by ensuring a recognizable feature of the tissue sample, e.g., the non-coronary sinus, is aligned the same for each sample, it is possible to ensure that all tissue samples are treated equally.

Software can control the automatic rotation of the chamber holders according to a desired schedule. Controllable parameters can include, for example, rotation direction, rotation time, rotation pause time, orbital shaking speed, orbital shaking time, orbital shaking pause time, and number of repetitions. By using a finely-controlled stepper motor and calculating rotations per minute by time rotated, the final resting degree of rotation can also be controlled.

Referring again to FIG. 14, each rotatable plate 515, 516 can be connected to a drive mechanism 517, 518, respectively that during use can rotate the plate 515, 516 causing the seeding chambers 514 to likewise rotate. The seeding chamber 514 held on the plate 515 in an upright orientation will rotate end over end during operation and the seeding chamber 514 held on the plate 516 will rotate in a axial rotation during operation. In general, the speed of rotation can be about 25 rpm or less, for instance from about 2 rpm to about 20 rpm.

Figure 16:
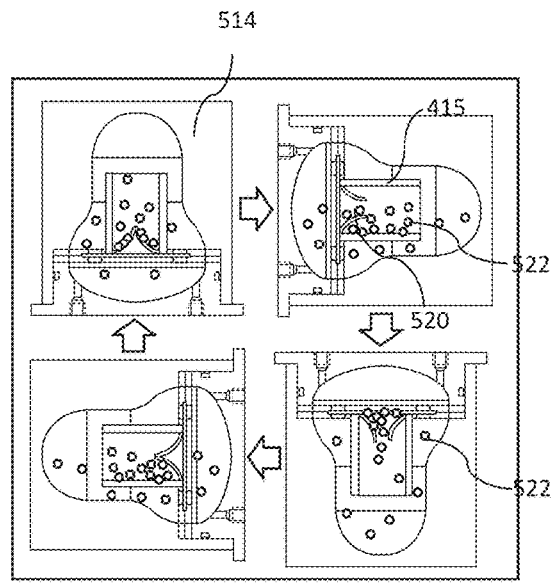
FIG. 16 illustrates a seeding chamber of the cell seeding apparatus of FIG. 14 in various orientations during seeding.

In one embodiment, the seeding chamber can be operated such that the seeding chamber 514 rotates completely. FIG. 16 illustrates this embodiment as a seeding chamber 514 is rotated in one complete rotation. This is not a requirement, however, and in other embodiments the seeding chamber can be operated such that the seeding chambers are rocked back and forth, without complete rotation.

The lid of the seeding chambers can include needless ports that can be used for changing media, adding cells, cycling the gas content, or any other access necessary. For example, to change media, a seeding chamber can be removed from the holder and transferred to a cell culture hood (FIG. 17C). The chamber can be drained by vacuum through a needleless port and replaced with sterile air. Following removal of all liquid, fresh media can be added to the chamber through a port. A vacuum can pull the media into the chamber, but is not necessarily required filling of a chamber. If additional gas exchange is desired, sterile filters can be attached to each needleless port and vacuum applied to one port. This can, e.g., draw $CO_2$ rich air into the seeding chamber.

Figure 15:
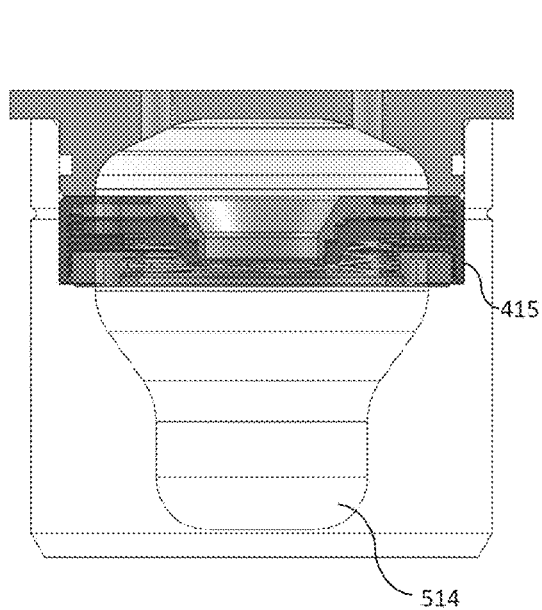
FIG. 15 illustrates a sectional view of a seeding chamber of the cell seeding apparatus of FIG. 14.

A scaffold to be seeded can be secured within a seeding chamber. FIG. 15 illustrates an exemplary seeding chamber 514 within which a tissue holder 415 has been secured. In FIG. 16, the seeding chamber including the tissue holder 415 is pictured with a heart valve tissue 520 held in the tissue holder. In one embodiment, the tissue to be seeded can have the cells applied interstitially and/or surface application to the tissue prior to placing the tissue in the seeding chamber. In another embodiment, the tissue can be contacted with the cells to be seeded thereon following location in the seeding chamber. For instance, and as illustrated in FIG. 16, a cell-containing liquid can be placed in the seeding chamber in conjunction with acellular heart valve tissue. As the seeding chamber rotates the cells 522 of the liquid wash continually over the tissues and adhere to the tissue during the operation or in a resting stage. Of course, a combination of methods can be utilized in which the tissue is seeded prior to placement in the seeding apparatus and the tissue is also contacted with a cell-containing fluid while held in the seeding apparatus.

In one embodiment, the cellular material can be gradually conditioned during the cell seeding process by slowly increasing the mechanical stress applied to the tissue. For instance, over the course of time, the rotational speed can be increased. Moreover, the cellular material can be initially rotated axially and following an initial conditioning period the tissue can be rotated in an end-over-end fashion, which can place increased mechanical stresses on portions of the tissue (for instance on the cusps of a heart valve).

Referring again to FIG. 14, the cell seeding apparatus can also be secured to agitator 530 that can agitate the cell seeding chambers 514 in conjunction with rotation. Rotation and agitation can be carried out throughout a cell seeding operation or periodically, as desired. For instance, rotation can be carried out for a period of time, such as from about 1 minute to about 1 hour followed by a period during which the cell seeding chambers do not rotate. Agitation can be carried out in conjunction with the rotation, during the period of no rotation, or both, as desired. Additionally, the speed of agitation can be increased over the course of the conditioning, similar to the speed and duration of rotation. During this time of conditioning, waste and nutritional gases can be exchanged or media can be changed as necessary.

Following the seeding and any preconditioning of the cellular material, the cellular material holder can be removed from the cell seeding chamber and secured in a bioreactor for further conditioning. Within the bioreactor, the cellular material (e.g., cell seeded tissue) can be subjected to physiological stresses to simulate the conditions to be expected in viva. According to one embodiment, the mechanical stresses placed on the cellular material in the bioreactor can be gradually increased so as to prevent loss of cells and/or loss of tissue integrity. Through gradual increase in pressure, shear stress, etc., the cellular material can slowly acclimate to physiological conditions. Previous studies have shown that cells will not remain attached to implant (e.g., heart valve) surfaces if shear forces are applied to the cells too rapidly. Thus, using the disclosed bioreactors, the flow, pressure, and fluid viscosity can be gradually increased to develop an appropriate pre-conditioning regime that allows the cells to maintain confluent coverage upon subjection to physiological conditions.

It is believed that progressively pre-conditioning cell seeded scaffolds in a disclosed bioreactor will allow internally seeded cells to migrate within the tissue and externally seeded cells to maintain confluent coverage.

Although in situ endothelialization of decellularized natural tissues such as valve cusps has been seen using various methodologies, full revitalization of the inner layers of the tissues has not been recorded after implantation. If proper cell-mediated maintenance of the tissue is to take place post-implantation, it will be necessary for cells to be present within the tissue prior to implantation. Injecting cells into the tissue has resulted in islands of cells within the tissue that need to spread out interstitially to repopulate the tissue. It is believed that this cell migration can be accomplished by subjecting the tissue to mechanical stimuli as available in the disclosed bioreactors. It is also likely that tissues will need to be endothelialised to allow for proper cellular communication from the surface cells to their interior counterparts. It is reasonable to infer that if cells can be retained on tissue surfaces in vitro at physiological levels of flow, pressure, and sheer stresses as obtainable in the disclosed bioreactors, then the cells will also remain attached to tissue surfaces upon in situ implantation.

Specific conditioning times, pressures, stroke volumes, etc. can vary depending upon the particular application, tissue type, and so forth to be conditioned within the bioreactor. For example, conditioning of a genetically engineered or bioprosthetic heart valve prior to implant can be carried out for a longer time as compared to the condition of a mechanical heart valve that has been surface seeded with cells. Likewise, a testing protocol may be run for a much longer time than is necessary for the conditioning of an implantable tissue prior to implant. The determination of such parameters for any particular application is well within the abilities of one of ordinary skill in the art and as such is not put forth in detail herein.

The present disclosure may be better understood with reference to the following Examples.

EXAMPLE 1

Fresh porcine aortic valve roots with ascending aorta up to the branching of the brachiocephalic artery were collected from adult pigs at a local abattoir. The valves were cleaned of fat and other extraneous tissues while maintaining a thin muscular shelf under the muscular cusp and a thin muscular layer 360° around the valve. Valves were decellularized by a 16-day perfusion technique and sterilized.

After decellularization, valves were crosslinked with pentagalloyl glucose (PGG) by treating with sterile 0.15% PGG in 50 mM dibasic sodium phosphate buffer in saline containing 20% isopropanol, pH 5.5. Treatment occurred at 22° C. on an orbital shaker for 21±1 hours. At the onset of fixation, cusps were lightly stuffed with sterile cotton balls pre-soaked in PGG solution to preserve the valve conformation in "closed" position. After treatment, the cotton balls were removed and the scaffolds were rinsed then stored in sterile 1× DPBS solution at 4° C.

Before cell seeding, valves were neutralized for 18-24 hours in DMEM with 50% FBS and 1% Antibiotics/Antimycotics at 37° C.

Following neutralization, the base and free edge of all cusps in each valve were inflated with sterile compressed aft (15-20 psi) attached to a sterile 33 G×1.25 inch needle. A sterile pipet was used to stabilize the tissue and the needle was inserted into the middle layer of the cusp, causing the fibrosa and ventricularis layers of the cusps to delaminate. Immediately after mixing, 4 million human adipose-derived stem cells (hADSCs) in 1 mL were loaded into a 1 mL syringe and manually injected into the free edges of the cusps in multiple areas and in the base of the cusp through a 33 G×1.25 inch needle. Injection was repeated for each cusp for a total of 12 million cells into the interstitial cusp area of each valve. Valves were then placed into a seeding chamber with the non-coronary sinus aligning with the 0° mark on the chamber (FIG. 18). The chamber was filled with enough cell culture media (DMEM with 10% FBS, 1% Antibiotic/Antimycotic) to cover the stainless steel mounting rings (about 120 mL). The chamber was closed as described above and placed into the end-over-end chamber holder on the Frame with the 0° chamber mark aligning to the corresponding mark on the end-over-end chamber holder.

After placing all the valves into the chamber holder, the shaker (VWR Model 3500 Standard Orbital Shaker) was at in line with both luer ports and also between two bolts; and on the third chamber, the 240° mark should be in line with both luer ports and also between two bolts. This can be achieved by rotating the lid in relation to the chamber body and will be important when using the axially rotating chamber holder plate.

The chamber was placed into the end-over-end holder on the frame with the 0° chamber mark aligning to the corresponding mark on the end-over-end chamber holder (position B in the table below). The chamber holder was positioned with the root up (position A in the table below) and the rotational regimen in the table below was followed for 15-20 hours).

| Position A (holder orientation) | Position B (rotation in holder) | Time (min) | Shaker Speed | Rotator Speed | Rotating Time (seconds) | Pause Time (seconds) | Cycles |
| --- | --- | --- | --- | --- | --- | --- | --- |
| Pre-Setting: Root Up | 0° on set mark | 00.13 | Off | 5.00 | 11 | 300 | 1 |
| Run for 12-15 seconds, then hit circular stop button during the first pause time. | | | | | | | |
| Rotating | 0° on set mark | 30.05 | 2 | 2.00 | 1805 | 5400 | 1 |
| Root Up + 30 degrees | 0° on set mark | 90.00 | Off | | | | |
| Rotating | 0° on set mark | 30.05 | 2 | | | | |
| Root Up + 330 degrees | 0° on set mark | 90.00 | Off | | | | |
| Run the above for 1 cycle = 4 hours. Be sure to turn shaker off/on as appropriate. | | | | | | | |
| Second pre-Setting | 0° on set mark | 00.03 | Off | 5.00 | 1 | 5400 | 1 |
| Run for 2-5 seconds, then hit circular stop button during the first pause time. | | | | | | | |
| Rotating | 0° on set mark | 15.30 | 2 | 1.00 | 930 | 6300 | 100 |
| Root Up + 180 degrees | 0° on set mark | 105.00 | Off | | | | |
| Rotating | 0° on set mark | 15.30 | 2 | | | | |
| Root Up | 0° on set mark | 105.00 | Off | | | | |
| Run the above until next seeding day. Can leave shaker off if needed. | | | | | | | | setting 2. The LabView program was set with the rotator at 5.0 RPM with a rotating time of 300 seconds and pause time of 300 seconds. Rotations alternated direction following each pause and the seeding chambers were rotated for 18-24 hours at 37° C. at those conditions to improve cell attachment to the valve scaffolds.

One day prior to internal seeding, the seeding chambers were assembled and filled with sterile 5% BSA in 1× DPBS to block attachment to the container and localize the future fibronectin/pronectin attachment to the valve. 24 hours later and immediately following the cell injection described above, the freshly internally injected valve scaffolds were coated with 4 µg/cm$^2$ (approximately 4 µg/mL) fibronectin or pronectin by adding the correct volume of fibronectin/pronectin to the culture media. Following interstitial cell seeding and coating with 4 µg/cm$^2$ fibronectin or pronectin, the exterior surfaces of the valves were seeded as described below.

30 million hADSCs were seeded over the course of three nights using end-over-end rotation of the valves. For this method, the seeding chamber was removed from the frame and drained. 10 million hADSCs were resuspended in 35 mL cell culture medium and added to the seeding chamber by use of a syringe, followed by about 90 mL of additional cell culture media to fill the chamber.

After or during attachment of the lid, each lid and associated chamber can be lined up in relation to the chamber body so that each degree mark (0, 120, and 240, FIG. 18) is each: 1) aligned with both luer ports and 2) between two bolts. For example, on the first chamber, the 0° mark should be in line with both luer ports and also between two bolts; on the second chamber, the 120° mark should be On the second day of seeding, the media was aspirated and another 10 million hADSCs were added to the chamber in 120 mL media through needleless ports. The seeding chamber was then placed back into the end-over-end holder on the frame with the 120° chamber mark aligning to the corresponding mark on the end-over-end chamber holder (position B). The chamber holder was positioned with the root up (position A) and the rotational regimen in the table above was followed for about 15-20 hours) with the only change being position B was at 120° on the set mark.

On the third day of seeding, the media was aspirated and another 10 million hADSCs were added to the chamber in 120 mL media through the needleless ports. The seeding chamber was then placed back into the end-over-end holder on the frame with the 240° chamber mark aligning to the corresponding mark on the end-over-end chamber holder (position B). The chamber holder was positioned with the root up (position A) and the rotational regimen in the table above was followed for about 15-20 hours) with the only change being position B was at 240° on the set mark.

Initial placement of cells by injection yielded boluses of cells in the free edges of the cusps because the cusp layers did not separate as easily in this location as they did in the base. The base of the cusp yielded the most complete air inflation. This allowed the injected cells to spread through the tissue more than in the free edges of the cusps. Overall, the method of injecting cells into the central layers of aortic cusps yielded an initial distribution of cells that was concentrated in boluses in various locations of the cusp. Cell migration and dynamic forces were relied on to cause these cells to spread throughout the tissue during culture.

Following rotational seeding, valves were analyzed immediately for cellular attachment, spreading, and alignment in comparison to fresh valve cusps. Analysis using Live/DEAD® imaging and scanning electron microscopy for the cusps revealed substantial recellularization. Many surfaces appeared to have as many cells present as the native cusps. The exception to this is seen in, where fewer cells are covering the ventricularis side of the cusp. However, during this trial of cell seeding, the rotational regimen was varied and the valve rested in the "root down" position for 5 minutes instead of 90 minutes. Since this is the position in which the ventricularis would have been seeded, this is likely the cause for less coverage here. Overall, initial cell repopulation of the cusps was very successful with this method with coverage matching that of the native cusps.

EXAMPLE 2

Following decellularization, sterilization, and crosslinking of valve matrix as described in Example 1, four valve roots were neutralized in 50% fetal bovine serum in DMEM with 1% antibiotic/antimycotic. The valves were then interstitially seeded as described in Example 1 with four million human adipose derived stem cells at no greater than passage 6 in 0.5 mL of cell culture media (DMEM with 10% FBS and 1% antibiotic/antimycotic) per cusp using direct and pre-inflation techniques. Immediately following interstitial seeding, the valves were coated with 4 µg/cm$^2$ of fibronectin or pronectin in cell culture media and externally seeded using three overnight rounds of 10 million human adipose derived stem cells at passage 6 in cell culture media in the cell seeding apparatus described herein (rotating end-over-end). Following the first round, as second round of external seeded was performed using three overnight rounds of 10 million human adipose derived stem cells at passage 7 in cell culture media in the cell seeding apparatus described herein (rotating about aorta central axis). One valve was taken at this point as an initially seeded control.

After the internal and external seeding, valves were conditioned further in the rotating chambers. The end-over-end rotating chamber holding plate was attached to the frame and needleless ports were attached to each seeding chamber. The chambers were placed into the chamber holder plate. Rotating and orbital conditions progressively increased every 12 hours until a shaker speed of 40% and rotational speed of 4 rpm were achieved for short-term conditioning. Position A (as described in Example 1) from previous rotation angles was not monitored from this point on. Media was changed every two days, daily, or every 12 hours as necessary based on pH colorimetric indicators in the media. After 5 days of rotational conditioning, valves were analyzed or transferred to the bioreactors for adaptive conditioning and testing.

After 5 days of the above rotational conditioning, distal aortic root stabilizers were added to each valve root for support during bioreactor conditioning and testing. Each valve was transferred to a pre-assembled bioreactor as illustrated in FIG. 6A. The valve conditions were increased to 25/15 mmHg at 75 beats per minute and a stroke volume of 35 mL over the course of eight days. Increases in pressure occurred every 12 hours. At each increase, systolic pressure was increased by 0.5 mmHg each time for the first five days and 4 mmHg each time for the final 3 days. Media was changed every 3.5 days (twice per week) throughout conditioning. Upon reaching final pressures of 25/15 mmHg and flow of 35 mL per stroke, valves were analyzed by Live/DEAD, histology, and immunohistochemistry.

It will be appreciated that the foregoing examples, given for purposes of illustration, are not to be construed as limiting the scope of this disclosure. Although only a few exemplary embodiments of the disclosed subject matter have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A bioreactor comprising:
   a circulatory flow path defined through the bioreactor:
   a module comprising a holder for cellular material removably locatable within the module, the holder dividing the module into an upper chamber and a lower chamber, the holder comprising a first plate and a second plate aligned with one another and defining a passage from a first side of the holder to a second side of the holder that passes through the aligned plates, the circulatory flow path passing into one of the upper chamber or the lower chamber, through the passage of the holder, and thence into the other of the upper or lower chamber prior to exiting the module;
   a pressure chamber separated from the lower chamber by a flexible membrane;
   a first compliance chamber, comprising a first end and a second, opposite end and a length between the first end and the second end defining an interior, wherein a cross-sectional area at the first end is larger than a cross-sectional area at the second end, the first end of the first compliance chamber comprising a first attachment for attaching the first compliance chamber to the circulatory flow path with the circulatory flow path in fluid communication with the interior of the first compliance chamber, the second end of the first compliance chamber being open to a surrounding atmosphere such that the interior of the first compliance chamber is in fluid communication with the surrounding atmosphere;
   a second compliance chamber comprising a first end and a second, opposite end and a length between the first end and the second end defining an interior, the first end of the second compliance chamber comprising a second attachment for attaching the second compliance chamber to the circulatory flow path with the circulatory flow path in fluid communication with the interior of the second compliance chamber, the second end of the second compliance chamber being sealed from the surrounding atmosphere such that the interior of the second compliance chamber is isolated from the surrounding atmosphere,
   a third attachment at which either the first compliance chamber or the second compliance chamber is attached via either the first attachment or the second attachment, respectively, to the circulatory flow path and thereby placed in fluid communication with the module via the circulatory flow path;
   wherein only one of the first compliance chamber or the second compliance chamber is alternatively attached to the circulatory flow path; and
   a reservoir in fluid communication with the circulatory flow path; wherein the circulatory flow path extends through the module, past the third attachment that is attached to either the first compliance chamber or the second compliance chamber, past or through the reservoir, and returns to the module.

2. The bioreactor of claim 1, wherein the first end of the first compliance chamber has a diameter of from about 0.25 inches to about 2 inches and the second end of the first compliance chamber has a diameter of from about 0.1 inches to about 1.5 inches.

3. The bioreactor of claim 1, the length of the first compliance chamber between the first end and the second end being about 2 inches or greater.

4. The bioreactor of claim 1, further comprising an air filter at the second end of the first compliance chamber.

5. The bioreactor of claim 1, the second compliance chamber including a smaller chamber within the second compliance chamber, the smaller chamber being in fluid communication with a source of an incompressible fluid.

6. The bioreactor of claim 1, further comprising a constriction valve in the circulatory flow path.

7. The bioreactor of claim 1, further comprising a reversible one-way valve in the circulatory flow path that allows for reversal of flow direction through the bioreactor.

8. A method for conditioning a cellular material comprising:
   securing a cellular material in the holder of the bioreactor of claim 1;
   attaching either the first compliance chamber or the second compliance chamber to the bioreactor at the third attachment; and
   establishing a pulsatile flow across the cellular material and along the circulatory flow path, the pulsatile flow being defined by characteristics including a stroke volume and a pressure differential that are at least partially established by the characteristics of the compliance chamber that is attached to the bioreactor.

9. The method of claim 8, wherein the cellular material comprises a heart valve.

10. The method of claim 8, wherein the cellular material has been decellularized.

11. The method of claim 10, further comprising seeding cells on the cellular material.

12. The method of claim 11, wherein the cells comprise stem cells.

13. The method of claim 11, wherein the cells are seeded on the cellular material prior to securing the cellular material in the holder.

14. The method of claim 13, further comprising pre-conditioning the cellular material following the cell seeding and prior to securing the cellular material in the holder.

15. The method of claim 8, wherein the stroke volume is from about 10 mL to about 200 mL.

16. The method of claim 8, wherein the stroke volume is from about 60 mL to about 80 mL.

17. The method of claim 8, wherein the pressure differential over a single pulse cycle is from about 2 mmHg to about 40 mmHg.

18. The method of claim 8, wherein the upper pressure of a single pulse cycle is from about 10 mmHg to about 45 mmHg.

19. The method of claim 18, wherein the lower pressure of a single pulse cycle is from about 5 mmHg to about 30 mmHg.

20. The method of claim 8, wherein the pressure differential over a single pulse cycle is from about 10 mmHg to about 150 mmHg.

21. The method of claim 8, wherein the upper pressure of a single pulse cycle is from about 70 mmHg to about 250 mmHg.

22. The method of claim 21, wherein the lower pressure of a single pulse cycle is from about 30 mmHg to about 150 mmHg.

23. The method of claim 8, further comprising altering the stroke volume and/or the pressure differential during the method, the alteration taking place without stopping the pulsatile flow across the cellular material.

* * * * *